(12) United States Patent
Pang et al.

(10) Patent No.: US 11,142,511 B2
(45) Date of Patent: Oct. 12, 2021

(54) COUMARIN OXIME ESTER COMPOUNDS, PREPARATION AND USE THEREOF

(71) Applicant: HUBEI GURUN TECHNOLOGY CO. LTD, Hubei (CN)

(72) Inventors: Yulian Pang, Beijing (CN); Yingquan Zou, Beijing (CN); Shuheng Fan, Beijing (CN); Ming Gao, Beijing (CN); Yangyang Xin, Beijing (CN)

(73) Assignee: Hubei Gurun Technology Co., Ltd., Jingmen (CN)

( * ) Notice: Subject to any disclaimer, the term of this patent is extended or adjusted under 35 U.S.C. 154(b) by 0 days.

(21) Appl. No.: 16/633,294

(22) PCT Filed: May 29, 2018

(86) PCT No.: PCT/CN2018/088830
§ 371 (c)(1),
(2) Date: Jan. 23, 2020

(87) PCT Pub. No.: WO2019/019792
PCT Pub. Date: Jan. 31, 2019

(65) Prior Publication Data
US 2020/0148660 A1    May 14, 2020

(30) Foreign Application Priority Data
Jul. 26, 2017    (CN) .......................... 201710620077.2

(51) Int. Cl.
*C07D 311/58*    (2006.01)
*C07D 493/04*    (2006.01)
*C08F 2/50*    (2006.01)

(52) U.S. Cl.
CPC .......... *C07D 311/58* (2013.01); *C07D 493/04* (2013.01); *C08F 2/50* (2013.01)

(58) Field of Classification Search
CPC .................................................. C07D 311/58
See application file for complete search history.

(56) References Cited

U.S. PATENT DOCUMENTS

2007/0037785 A1 *    2/2007   Ansorge ................ C07C 311/08
514/183

OTHER PUBLICATIONS

Merchant et al., "An interesting, etc.," Current Science, 47 (7), pp. 228-229. (Year: 1978).*
RN 1193324-99-0 (Registry, STN) Nov. 23, 2009.*
RN 1045578-17-3 (Registry, STN) Sep. 1, 2008.*
RN 861977-24-4 (Registry, STN) Aug. 29, 2005.*

* cited by examiner

*Primary Examiner* — Patricia L Morris
(74) *Attorney, Agent, or Firm* — Kilpatrick Townsend & Stockton LLP

(57) ABSTRACT

The present invention relates to a coumarin (keto) oxime ester compound of formula (I), wherein n and $R_1$, $R_2$, $R_3$, $R_4$, $R_5$, $R_6$, and $R_7$ are as defined in the specification. The compound has strong ultraviolet absorption in the range of 300 to 450 nm. After absorbing light energy, it can quickly transfer energy and continuously initiate polymerization. It has obvious advantages in terms of photosensitivity and pattern integrity, and is very suitable for radiation curing by UV-LED light source. In addition, the compound of formula (I) also has good thermal stability. The present invention also relates to a method for preparing the compound of formula (I) and use of the compound. The compound is suitable as a photoinitiator in a UV-LED light curing system and is suitable for the radiation wavelength of UV-LED light curing.

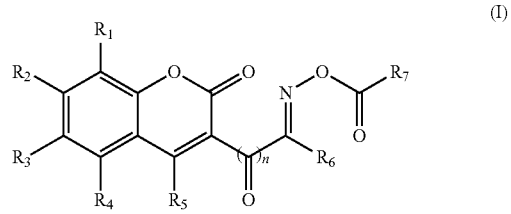

(I)

8 Claims, 1 Drawing Sheet

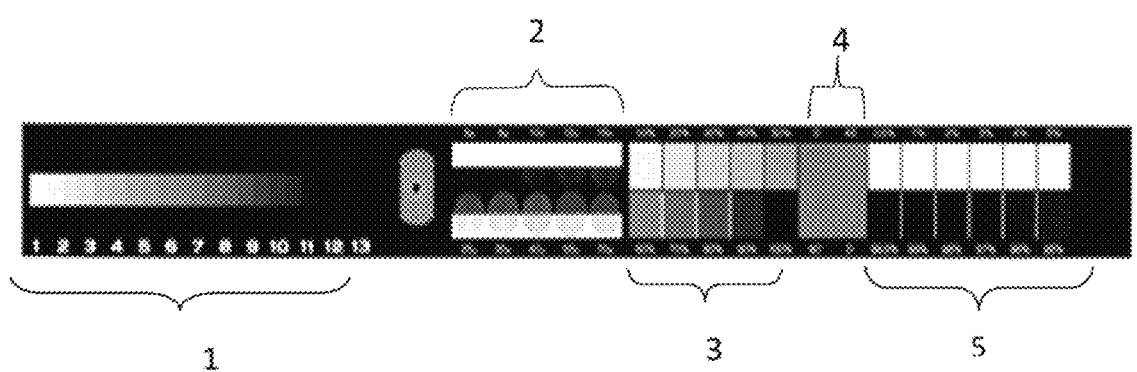

COUMARIN OXIME ESTER COMPOUNDS, PREPARATION AND USE THEREOF

FIELD OF THE INVENTION

The present invention relates to coumarin 3-ketooxime ester compounds, which can be used as a photoinitiator. The present invention also relates to the preparation and use of coumarin 3-ketooxime ester compounds.

BACKGROUND OF THE INVENTION

Photoinitiators, also known as photosensitizers or photo-curing agents, are a class of compounds that can absorb energy of a certain wavelength in the ultraviolet region (250-400 nm) or visible region (400-600 nm) to generate free radicals, cations, etc., thereby initiating monomer polymerization, crosslinking and curing. In the photo-curing system, the photoinitiator generally accounts for 3-5%. Although the content is low, it is the key component among them, which plays a decisive role in the photo-curing speed. It is related to whether the oligomer and diluent can be rapidly cross-linked and solidified when the formula system is irradiated with light, thereby changing from liquid to solid. At present, light curing technology has been widely used in traditional fields such as coatings, inks, microelectronics, printing, etc. In addition, it is also used in new fields such as the preparation of laser video and three-dimensional components. As an important component of the photo-curing system, the photoinitiator must meet the requirements of different photo-curing conditions and applications. In the field of free radical photoinitiators, the main goals are: to improve light sensitivity, improve surface curing efficiency (anti-oxidation inhibition), improve deep curing performance, improve solubility of photoinitiators in monomers and resins, reduce toxicity and odor, reduce migration of uncured initiator after curing, and reduce yellowing.

Oxime ester photoinitiators have become a class of photoinitiators that have received increasing attention in recent years because of their excellent photosensitivity, wherein BASF's products OXE-01 and OXE-02 are two typical oxime esters currently on the market. These two products have high photosensitivity, but their UV absorption wavelengths are relatively short and are not suitable for the needs of UV-LED light sources (emission wavelength of 365 nm, 385 nm, 395 nm, 405 nm, and 420 nm). There are also some Chinese patents on oxime ester photoinitiators. For example, CN102775527A discloses a diphenyl sulfide ketone oxime ester photoinitiator and a preparation method thereof. CN102492059A discloses substituted diphenyl sulfide ketoxime type photoinitiators and the like. However, the ultraviolet absorption wavelength of most initiators is 250-350 nm, which cannot match with the increasingly developed LED light sources, and greatly limits the application of oxime ester photoinitiators.

CN104817653A discloses an oxime ester photoinitiator suitable for UV-LED light source curing. The initiator compound is a coumarin aldoxime ester compound. However, studies have shown that the thermal stability of such compounds is less than that of OXE-01. [Zhu Guigang, Synthesis of coumarin oxime ester derivatives and their application in LED light curing, Master thesis, 2016; Dietliker K, Birbaum J L, Hüsler R, et al. Photolatent catalysts [J]. CHIMIA International Journal for Chemistry, 2002, 56(5): 197-202.]

CN1889960A discloses that coumarinone oxime ester compounds can be used in pharmaceutical or cosmetic compositions to prevent and treat diseases, including immunological diseases, chronic inflammation, neurological and skin diseases, tumor diseases, specific viruses (particularly SARS) and so on. In this sense, such compounds are safe and non-toxic, but no literature has reported the use of coumarin ketoxime esters as photoinitiators.

Therefore, there is still a need for a photoinitiator with an absorption wavelength suitable for UV-LED light sources (emission wavelength of 300 to 450 nm, especially 365 to 420 nm) and good thermal stability.

SUMMARY OF THE INVENTION

In view of the problems existing in the prior art, the inventors of the present invention have conducted extensive and in-depth research on photoinitiators suitable for radiation curing by UV-LED light sources (emission wavelength of 300 to 450 nm, especially 365 to 420 nm) in order to find a photoinitiator that can replace OXE-01 and OXE-02, which can be more suitable for UV-LED light source curing and has good thermal stability. The inventors of the present invention have found that the coumarin (keto) oxime ester compounds obtained by connecting an unsubstituted or substituted coumarin directly or via a carbonyl group to an oxime ester moiety have strong ultraviolet absorption in the range of 300 to 450 nm, especially 350 to 420 nm, and have good thermal stability, so they are suitable as photoinitiators for radiation curing by UV-LED light source. The objects of the present invention are achieved based on the foregoing findings.

Therefore, an object of the present invention is to provide a coumarin (keto) oxime ester compound, whose absorption wavelength is not only suitable for Radiation curing by UV-LED light source, but also has good thermal stability.

Another object of the present invention is to provide a method for preparing the coumarin (keto) oxime ester compound of the present invention.

Another object of the present invention is to provide use of the coumarin (keto) oxime ester compound of the present invention as a photoinitiator or a photosensitizer.

The technical solutions to achieve the above-mentioned objects of the present invention can be summarized as follows:

1. A coumarin (keto) oxime ester compound of formula (I):

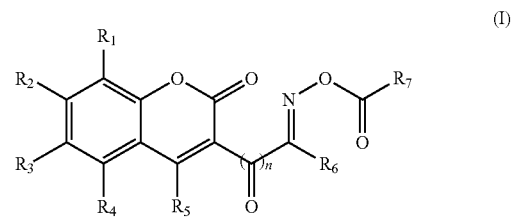

wherein:
n is 0 or 1;
$R_1$, $R_2$, $R_3$, $R_4$, and $R_5$ independently represent hydrogen, halogen, nitro, hydroxy, mercapto, carboxyl, $C_1$-$C_8$ carboxylate ester group, sulfonic acid group, amino, cyano, $C_1$-$C_{20}$ alkyl, $C_2$-$C_{20}$ alkenyl, $C_2$-$C_{20}$ alkynyl, $C_3$-$C_{20}$ cycloalkyl, $C_4$-$C_{20}$ cycloalkylalkyl, $C_1$-$C_{20}$ alkoxy, $C_2$-$C_{20}$ alkenyloxy, $C_2$-$C_{20}$ alkynyloxy, $C_3$-$C_{20}$ cycloalkoxy, $C_4$-$C_{20}$ cycloalkylalkoxy, $C_1$-$C_{20}$ alkylthio, $C_2$-$C_{20}$ alkenylthio, $C_2$-$C_{20}$ alkynylthio, $C_3$-$C_{20}$ cycloalkylthio, $C_4$-$C_{20}$ cycloalkylalkylthio, $C_6$-$C_{18}$ aryl, $C_6$-$C_{18}$ aryloxy and $C_6$-$C_{18}$ arylthio, wherein the aforementioned amino, $C_1$-$C_{20}$ alkyl, $C_2$-$C_{20}$ alkenyl, $C_2$-$C_{20}$ alkynyl, $C_3$-$C_{20}$ cycloalkyl, $C_4$-$C_{20}$ cycloalkylalkyl, $C_1$-$C_{20}$ alkoxy, $C_2$-$C_{20}$ alkenyloxy, $C_2$-$C_{20}$ alkynyloxy, $C_3$-$C_{20}$ cycloalkoxy, $C_4$-$C_{20}$ cycloalkylalkoxy, $C_1$-$C_{20}$ alkylthio, $C_2$-$C_{20}$ alkenylthio, $C_2$-$C_{20}$ alkynylthio, $C_3$-$C_{20}$ cycloalkylthio, $C_4$-$C_{20}$ cycloalkylalkylthio, $C_6$-$C_{18}$ aryl, $C_6$-$C_{18}$ aryloxy and $C_6$-$C_{18}$ arylthio may be optionally substituted with one or more groups independently selected from the group consisting of halogen, nitro, hydroxy, mercapto, carboxyl, sulfonic acid group, amino, cyano, $C_1$-$C_6$ alkyl, $C_1$-$C_6$ alkoxy, $C_1$-$C_6$ alkylthio, $C_2$-$C_6$ alkenyl and $C_2$-$C_6$ alkynyl, or $R_1$ together with $R_2$, $R_2$ together with $R_3$, $R_3$ together with $R_4$, or $R_1$ together with $R_2$ and $R_3$ together with $R_4$ form a saturated or unsaturated divalent group having 3 to 4 atoms selected from C, N, O, and S and wherein at least one of the atoms is carbon atom; and $R_6$ and $R_7$ independently represent linear or branched $C_1$-$C_{20}$ alkyl, $C_3$-$C_{10}$ cycloalkyl, $C_4$-$C_{10}$ cycloalkylalkyl, $C_4$-$C_{10}$ alkylcycloalkyl, $C_6$-$C_{20}$ aryl, $C_7$-$C_{20}$ aralkyl and $C_7$-$C_{20}$ alkylaryl, wherein the aforementioned $C_1$-$C_{20}$ alkyl, $C_3$-$C_{10}$ cycloalkyl, $C_4$-$C_{10}$ cycloalkylalkyl, $C_4$-$C_{10}$ alkylcycloalkyl, $C_6$-$C_{20}$ aryl, $C_7$-$C_{20}$ aralkyl and $C_7$-$C_{20}$ alkylaryl may be optionally substituted with one or more groups independently selected from the group consisting of: $C_1$-$C_6$ alkyl, $C_1$-$C_6$ alkylthio, $C_1$-$C_6$ alkoxy, halogen, nitro, amino, mono($C_1$-$C_6$ alkyl)amino, di($C_1$-$C_6$ alkyl)amino and mercapto, except for the compound that meets the following definitions: n is 0, $R_1$, $R_2$, $R_3$, $R_4$ and $R_5$ are all H, $R_6$ is methyl, and $R_7$ is n-propyl.

2. The compound according to item 1, wherein $R_1$, $R_2$, $R_3$, $R_4$, and $R_5$ are independently selected from hydrogen, halogen, nitro, hydroxy, mercapto, carboxyl, $C_1$-$C_6$ carboxylate ester group, sulfonic acid group, amino, cyano, $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkylalkyl, $C_1$-$C_6$ alkoxy, $C_2$-$C_6$ alkenyloxy, $C_2$-$C_6$ alkynyloxy, $C_3$-$C_8$ cycloalkoxy, $C_4$-$C_8$ cycloalkylalkoxy, $C_1$-$C_6$ alkylthio, $C_2$-$C_6$ alkenylthio, $C_2$-$C_6$ alkynylthio, $C_3$-$C_8$ cycloalkylthio, $C_4$-$C_8$ cycloalkylalkylthio, $C_6$-$C_{10}$ aryl, $C_6$-$C_{10}$ aryloxy and $C_6$-$C_{10}$ arylthio, wherein the aforementioned amino, $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkylalkyl, $C_1$-$C_6$ alkoxy, $C_2$-$C_6$ alkenyloxy, $C_2$-$C_6$ alkynyloxy, $C_3$-$C_8$ cycloalkoxy, $C_4$-$C_8$ cycloalkylalkoxy, $C_1$-$C_6$ alkylthio, $C_2$-$C_6$ alkenylthio, $C_2$-$C_6$ alkynylthio, $C_3$-$C_8$ cycloalkylthio, $C_4$-$C_8$ cycloalkylalkylthio, $C_6$-$C_{10}$ aryl, $C_6$-$C_{10}$ aryloxy and $C_6$-$C_{10}$ arylthio may be optionally substituted with one or more groups independently selected from the group consisting of: halogen, nitro, hydroxy, mercapto, carboxyl, sulfonic acid group, amino, cyano, $C_1$-$C_4$ alkyl, $C_1$-$C_4$ alkoxy, $C_1$-$C_4$ alkylthio, $C_2$-$C_4$ alkenyl and $C_2$-$C_4$ alkynyl; or, $R_1$ together with $R_2$, $R_2$ together with $R_3$, or $R_3$ together with $R_4$ form a saturated or unsaturated divalent group having 3 to 4 atoms selected from C, N, O, and S and wherein at least one of the atoms is carbon atom, preferably, $R_1$, $R_2$, $R_3$, $R_4$, and $R_5$ are independently selected from hydrogen, halogen, nitro, $C_1$-$C_4$ carboxylate ester group, $C_1$-$C_4$ alkyl, $C_2$-$C_4$ alkenyl, $C_1$-$C_4$ alkoxy, $C_1$-$C_4$ alkylthio, mono($C_1$-$C_4$ alkyl)amino, di($C_1$-$C_4$ alkyl)amino, phenoxy and phenylthio; or, $R_1$ together with $R_2$, $R_2$ together with $R_3$, or $R_3$ together with $R_4$ form a saturated or unsaturated divalent group having 3 to 4 atoms selected from C, N, O, and S and wherein at least one of the atoms is carbon atom, for example, —O—$CH_2$—O—, —S—$CH_2$—S—, —N—$CH_2$—N—, —O—$CH_2CH_2$—O—, —S—$CH_2CH_2$—S—, —N—$CH_2CH_2$—N— or —CH=CH—CN=CH—.

3. The compound according to item 1 or 2, wherein $R_6$ and $R_7$ independently represent linear or branched $C_1$-$C_8$ alkyl, $C_3$-$C_8$ cycloalkyl, $C_4$-$C_8$ cycloalkylalkyl, $C_4$-$C_8$ alkylcycloalkyl, $C_6$-$C_{10}$ aryl, $C_7$-$C_{11}$ aralkyl and $C_7$-$C_{11}$ alkylaryl, wherein the aforementioned $C_1$-$C_8$ alkyl, $C_3$-$C_8$ cycloalkyl, $C_4$-$C_8$ cycloalkylalkyl, $C_4$-$C_8$ alkylcycloalkyl, $C_6$-$C_{10}$ aryl, $C_7$-$C_{11}$ aralkyl and $C_7$-$C_{11}$ alkylaryl may be optionally substituted with one or more groups independently selected from the group consisting of: $C_1$-$C_4$ alkyl, $C_1$-$C_4$ alkylthio, $C_1$-$C_4$ alkoxy, halogen, nitro, amino, mono($C_1$-$C_4$ alkyl)amino, di($C_1$-$C_4$ alkyl)amino and mercapto, preferably, $R_6$, and $R_7$ are independently selected from linear or branched $C_1$-$C_8$ alkyl, $C_5$-$C_6$ cycloalkyl, $C_1$-$C_4$ alkyl substituted with $C_5$-$C_6$ cycloalkyl, $C_1$-$C_4$ alkyl substituted with phenyl, and phenyl, wherein the aforementioned phenyl each may be optionally substituted with one or more groups independently selected from the group consisting of: $C_1$-$C_4$ alkyl, $C_1$-$C_4$ alkylthio, $C_1$-$C_4$ alkoxy, halogen, nitro, amino, mono($C_1$-$C_4$ alkyl)amino, di($C_1$-$C_4$ alkyl)amino and mercapto;

more preferably, $R_6$ is linear or branched $C_1$-$C_6$ alkyl, $C_5$-$C_6$ cycloalkyl, $C_1$-$C_2$ alkyl substituted with $C_5$-$C_6$ cycloalkyl, or phenyl, and the aforementioned phenyl may be optionally substituted with one or more groups independently selected from the group consisting of: $C_1$-$C_4$ alkyl, $C_1$-$C_4$ alkylthio, $C_1$-$C_4$ alkoxy, halogen, nitro, amino and mercapto, and $R_7$ is linear or branched $C_1$-$C_7$ alkyl or phenyl, wherein the phenyl may be optionally substituted with one or more groups independently selected from the group consisting of: $C_1$-$C_4$ alkyl, halogen, nitro, amino, mono($C_1$-$C_4$ alkyl) amino, di($C_1$-$C_4$ alkyl)amino and mercapto.

4. The compound according to any one of items 1 to 3, wherein $R_5$ is H.

5. The compound according to item 1 or 4, wherein n is 0, $R_1$, $R_2$, $R_3$, and $R_4$ are independently selected from hydrogen, halogen, nitro, $C_1$-$C_4$ carboxylate ester group, $C_1$-$C_6$ alkyl, $C_2$-$C_4$ alkenyl, $C_1$-$C_4$ alkoxy, $C_1$-$C_4$ alkylthio, mono($C_1$-$C_4$ alkyl)amino, di($C_1$-$C_4$ alkyl)amino, phenoxy and phenylthio; or, $R_1$ together with $R_2$, $R_2$ together with $R_3$, or $R_3$ together with $R_4$ form a saturated or unsaturated divalent group having 3 to 4 atoms selected from C, N, O, and S and wherein at least one of the atoms is carbon atom, for example, —CH=CH—CN=CH—;

$R_6$ is linear or branched $C_1$-$C_6$ alkyl, halo $C_1$-$C_6$ alkyl, $C_5$-$C_6$ cycloalkyl, $C_1$-$C_2$ alkyl substituted with $C_5$-$C_6$ cycloalkyl, or phenyl, and the aforementioned phenyl may be optionally substituted with one or more groups independently selected from the group consisting of: fluorine, chlorine, bromine, $C_1$-$C_4$ alkyl, $C_1$-$C_4$ alkoxy, $C_1$-$C_4$ alkylthio and halo $C_1$-$C_4$ alkyl, and $R_7$ is linear or branched $C_1$-$C_7$ alkyl or phenyl, wherein the phenyl may be optionally substituted with one or more groups independently selected from the group consisting of: $C_1$-$C_4$ alkyl, halogen, nitro, amino, mono($C_1$-$C_4$ alkyl)amino and di($C_1$-$C_4$ alkyl)amino, or n is 1, $R_1$, $R_2$, $R_3$, and $R_4$ are independently selected from hydrogen, $C_1$-$C_4$ alkyl, $C_1$-$C_4$ alkoxy, $C_1$-$C_4$ alkylthio, mono ($C_1$-$C_4$ alkyl)amino, di($C_1$-$C_4$ alkyl)amino, phenoxy and phenylthio; or, $R_1$ together with $R_2$, $R_2$ together with $R_3$, or $R_3$ together with $R_4$ form a saturated or unsaturated divalent group having 3 to 4 atoms selected from C, N, O, and S and wherein at least one of the atoms is carbon atom, for example, —O—CH$_2$—O—, —S—CH$_2$—S—, —N—CH$_2$—N—, —O—CH$_2$CH$_2$—O—, —S—CH$_2$CH$_2$—S— or —N—CH$_2$CH$_2$—N;

$R_6$ is linear or branched $C_1$-$C_6$ alkyl, halo $C_1$-$C_6$ alkyl, $C_5$-$C_6$ cycloalkyl or $C_1$-$C_2$ alkyl substituted with $C_5$-$C_6$ cycloalkyl, and $R_7$ is linear or branched $C_1$-$C_6$ alkyl or phenyl optionally substituted with nitro.

6. The compound according to item 1, wherein the compound of formula (I) is selected from compounds 1 to 50.

7. A method for preparing the compound according to any one of items 1 to 6, comprising the steps of:

(1) oximation reaction: when n is 0, a compound of formula (II) is subjected to oximation reaction with hydroxylamine and/or hydroxylamine hydrochloride to obtain a compound of formula (IIIa)

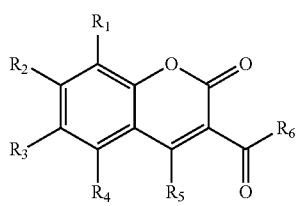

when n is 1, a compound of formula (II) is subjected to oximation reaction with a reagent selected from the group consisting of nitrous acid, nitrite and alkyl nitrite to obtain a compound of formula (IIIb):

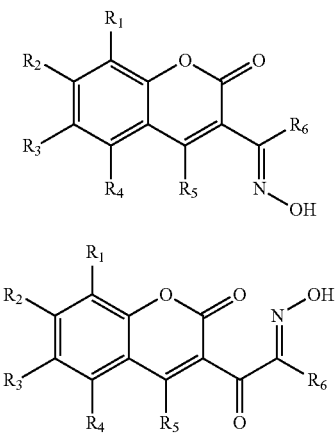

wherein $R_1$-$R_5$ and $R_6$ in formulae (II), (IIIa) and (IIIb) are as defined in any one of items 1 to 6; and (2) the compound of formula (IIIa) or (IIIb) is esterified to obtain the compound of formula (I).

8. The method according to item 7, wherein when n is 0: the oximation reaction is performed in the presence of sodium acetate, pyridine, piperidine, triethylamine or a mixture thereof; and/or, the oximation reaction is performed in the presence of ethanol or aqueous ethanol as solvent; and/or, the temperature of oximation reaction is 60 to 120° C.; and/or, the time of oximation reaction is 0.1 to 20 hours, preferably 0.5 to 10 hours; and a molar ratio of the compound of formula (II) to the compound selected from hydroxylamine and/or hydroxylamine hydrochloride is 1:1.5 to 1.5:1, preferably 1:1.2 to 1.2:1;

when n is 1, the oximation reaction is performed in the presence of concentrated hydrochloric acid; and/or, the oximation reaction is performed in the presence of ethanol or aqueous ethanol as solvent; and/or, the temperature of oximation reaction is −30 to 20° C., preferably 5 to 20° C.; and/or, the time of oximation reaction is 0.1 to 20 hours, preferably 0.5 to 10 hours; and a molar ratio of the compound of formula (II) to the compound selected from nitrous acid, nitrite and/or alkyl nitrite is 1:1.5 to 1.5:1, preferably 1:1.2 to 1.2:1;

9. The method according to item 7 or 8, wherein the alkyl nitrite is $C_1$-$C_6$ alkyl nitrite, for example, methyl nitrite, ethyl nitrite, isopropyl nitrite, butyl nitrite, isoamyl nitrite; and/or, the esterification of step (2) is performed using an esterifying agent selected from compounds of the following formulae (IVa), (IVb) and (IVc):

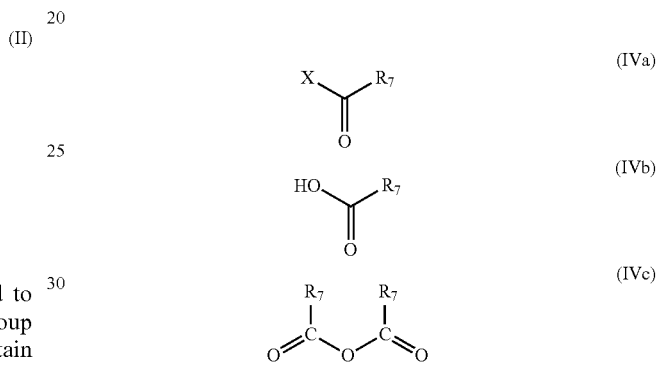

wherein X is halogen, especially chlorine, and $R_7$ is as defined in any one of items 1 to 6.

10. The method according to any one of items 7 to 9, wherein the esterification reaction is performed in the presence of one or more catalysts selected from the group consisting of: sulfuric acid, perchloric acid, zinc chloride, ferric chloride, pyridine, p-toluenesulfonic acid, sodium hydroxide, potassium hydroxide, sodium carbonate, sodium bicarbonate, sodium tert-butoxide, sodium ethoxide, sodium hydride, potassium hydride, calcium hydride and tertiary amines, for example, trialkylamine, such as trimethylamine and triethylamine.

11. The method according to any one of items 7 to 10, wherein the esterification reaction is performed in a solvent selected from the group consisting of tetrahydrofuran, benzene, toluene, N,N-dimethylformamide, dichloromethane and acetone; and/or, a molar ratio of the compound of formula (IIIa) or formula (IIIb) to the esterifying agent selected from the compounds of (IVa), (IVb) and (IVc) is 1:1.5 to 1.5:1, preferably 1:1.2 to 1.2:1.

12. Use of the compound of formula (I) according to any one of items 1 to 6 as a photoinitiator, especially as a photoinitiator in a UV-LED light curing system, particularly use as a photoinitiator or photosensitizer in a photo-curing system with a radiation wavelength of 300 to 450 nm, preferably 350 to 420 nm, especially 365 to 405 nm.

BRIEF DESCRIPTION OF THE DRAWINGS

FIG. 1 is a schematic diagram of a Ugra offset plate test strip, in which

1—Continuous density scale section,

2—Dark-bright micron isoline concentric circle section,

3—Full-tone dot section,
4—Ghosting control section, and
5—Highlight, shadow control section.

DETAILED DESCRIPTION OF THE INVENTION

According to a first aspect of the present invention, a coumarin (keto) oxime ester compound of the following formula (I) is provided:

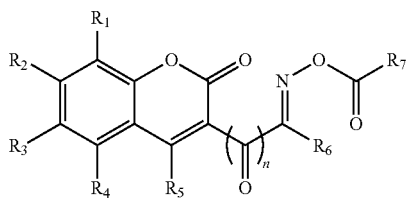

(I)

wherein:

n is 0 or 1;

$R_1$, $R_2$, $R_3$, $R_4$, and $R_5$ independently represent hydrogen, halogen, nitro, hydroxy, mercapto, carboxyl, $C_1$-$C_8$ carboxylate ester group, sulfonic acid group, amino, cyano, $C_1$-$C_{20}$ alkyl, $C_2$-$C_{20}$ alkenyl, $C_2$-$C_{20}$ alkynyl, $C_3$-$C_{20}$ cycloalkyl, $C_4$-$C_{20}$ cycloalkylalkyl, $C_1$-$C_{20}$ alkoxy, $C_2$-$C_{20}$ alkenyloxy, $C_2$-$C_{20}$ alkynyloxy, $C_3$-$C_{20}$ cycloalkoxy, $C_4$-$C_{20}$ cycloalkylalkoxy, $C_1$-$C_{20}$ alkylthio, $C_2$-$C_{20}$ alkenylthio, $C_2$-$C_{20}$ alkynylthio, $C_3$-$C_{20}$ cycloalkylthio, $C_4$-$C_{20}$ cycloalkylalkylthio, $C_6$-$C_{18}$ aryl, $C_6$-$C_{18}$ aryloxy and $C_6$-$C_{18}$ arylthio, wherein the aforementioned amino, $C_1$-$C_{20}$ alkyl, $C_2$-$C_{20}$ alkenyl, $C_2$-$C_{20}$ alkynyl, $C_3$-$C_{20}$ cycloalkyl, $C_4$-$C_{20}$ cycloalkylalkyl, $C_1$-$C_{20}$ alkoxy, $C_2$-$C_{20}$ alkenyloxy, $C_2$-$C_{20}$ alkynyloxy, $C_3$-$C_{20}$ cycloalkoxy, $C_4$-$C_{20}$ cycloalkylalkoxy, $C_1$-$C_{20}$ alkylthio, $C_2$-$C_{20}$ alkenylthio, $C_2$-$C_{20}$ alkynylthio, $C_3$-$C_{20}$ cycloalkylthio, $C_4$-$C_{20}$ cycloalkylalkylthio, $C_6$-$C_{18}$ aryl, $C_6$-$C_{18}$ aryloxy and $C_6$-$C_{18}$ arylthio may be optionally substituted with one or more groups independently selected from the group consisting of halogen, nitro, hydroxy, mercapto, carboxyl, sulfonic acid group, amino, cyano, $C_1$-$C_6$ alkyl, $C_1$-$C_6$ alkoxy, $C_1$-$C_6$ alkylthio, $C_2$-$C_6$ alkenyl and $C_2$-$C_6$ alkynyl, or $R_1$ together with $R_2$, $R_2$ together with $R_3$, $R_3$ together with $R_4$, or $R_1$ together with $R_2$ and $R_3$ together with $R_4$ form a saturated or unsaturated divalent group having 3 to 4 atoms selected from C, N, O, and S and wherein at least one of the atoms is carbon atom; and $R_6$ and $R_7$ independently represent linear or branched $C_1$-$C_{20}$ alkyl, $C_3$-$C_{10}$ cycloalkyl, $C_4$-$C_{10}$ cycloalkylalkyl, $C_4$-$C_{10}$ alkylcycloalkyl, $C_6$-$C_{20}$ aryl, $C_7$-$C_{20}$ aralkyl and $C_7$-$C_{20}$ alkylaryl, wherein the aforementioned $C_1$-$C_{20}$ alkyl, $C_3$-$C_{10}$ cycloalkyl, $C_4$-$C_{10}$ cycloalkylalkyl, $C_4$-$C_{10}$ alkylcycloalkyl, $C_6$-$C_{20}$ aryl, $C_7$-$C_{20}$ aralkyl and $C_7$-$C_{20}$ alkylaryl are optionally substituted with one or more groups independently selected from the group consisting of: $C_1$-$C_6$ alkyl, $C_1$-$C_6$ alkylthio, $C_1$-$C_6$ alkoxy, halogen, nitro, amino, mono ($C_1$-$C_6$ alkyl)amino, di($C_1$-$C_6$ alkyl)amino and mercapto, except for the compound that meets the following definitions: n is 0, $R_1$, $R_2$, $R_3$, $R_4$ and $R_5$ are all H, $R_6$ is methyl, and $R_7$ is n-propyl.

The compound of formula (I) contains both a coumarin-based structural moiety and a (keto) oxime ester-based structural moiety. The compound has strong ultraviolet absorption in the range of 300 to 450 nm. After absorbing light energy, it can quickly transfer energy and continuously initiate polymerization. It has obvious advantages in terms of photosensitivity and pattern integrity, and is very suitable for UV-LED light source, and it is safe and non-toxic and can be used in food packaging and other fields. In addition, the compound of formula (I) also has good thermal stability.

In the present invention, the prefix "$C_n$-$C_m$" means in each case that the number of carbon atoms contained in the group is n to m.

"Halogen" means fluorine, chlorine, bromine, and iodine. In the present invention, preferably, the halogen includes F, Cl, or a combination thereof.

As used herein, the term "$C_n$-$C_m$ alkyl" refers to a branched or unbranched saturated hydrocarbon group having n to m carbon atoms, such as 1 to 20, preferably 1 to 12, more preferably 1 to 8, particularly preferably 1 to 6, and particularly preferably 1 to 4 carbon atoms, for example, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl, decyl, undecyl, dodecyl, and isomers thereof. $C_1$-$C_8$ alkyl can be methyl, ethyl, propyl, isopropyl, n-butyl, 2-butyl, tert-butyl, pentyl, isopentyl, hexyl, heptyl, octyl, and isomers thereof. $C_1$-$C_6$ alkyl can be methyl, ethyl, propyl, isopropyl, n-butyl, 2-butyl, tert-butyl, pentyl, isopentyl, hexyl, and isomers thereof. $C_1$-$C_4$ alkyl can be methyl, ethyl, propyl, 1-methylethyl, butyl, 1-methylpropyl, 2-methylpropyl, 1,1-dimethylethyl, and isomers thereof.

As used herein, the term "$C_2$-$C_m$ alkenyl" refers to a branched or unbranched unsaturated open-chain hydrocarbon group having 2 to m, such as 2 to 20, preferably 2 to 6, more preferably 2 to 4 carbon atoms and having one or more double bonds at any position, for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, and isomers thereof. $C_2$-$C_6$ alkenyl can be ethenyl, propenyl, 1-butenyl, 2-butenyl, isobutenyl, 1-pentenyl, 2-pentenyl, neopentenyl, 1-hexenyl, 2-hexenyl, 3-hexenyl, isohexenyl, neohexenyl, and isomers thereof. $C_2$-$C_4$ alkenyl can be ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, and isomers thereof.

As used herein, the term "$C_2$-$C_m$ alkynyl" refers to a branched or unbranched unsaturated open-chain hydrocarbon group having 2 to m, such as 2 to 20, preferably 2 to 6, more preferably 2 to 4 carbon atoms and having one or more triple bonds at any position, for example, ethynyl, propynyl, 1-butynyl, 2-butynyl, and isomers thereof. $C_2$-$C_6$ alkynyl can be ethynyl, propynyl, 1-butynyl, 2-butynyl, 1-pentynyl, 2-pentynyl, 3-pentynyl, 4-pentynyl, 1-hexynyl, 2-hexynyl, 3-hexynyl, 4-hexynyl, 5-hexynyl, and isomers thereof. $C_2$-$C_4$ alkynyl can be ethynyl, propynyl, 1-butynyl, 2-butynyl, and isomers thereof.

As used herein, the term "$C_3$-$C_m$ cycloalkyl" refers to a saturated alicyclic monocyclic group having 3 to m, such as 3 to 20, preferably 3 to 8, more preferably 5 to 6 ring carbon atoms, for example, cyclopropyl, cyclobutyl, cyclopentyl, cyclohexyl, cycloheptyl, cyclooctyl and cyclodecyl.

The term "$C_4$-$C_m$ cycloalkylalkyl" means an alkyl group substituted with a cycloalkyl group and contains a total of 4 to m carbon atoms, such as 4 to 20 carbon atoms, preferably 4 to 10 carbon atoms, more preferably 4 to 6 carbon atoms, wherein the alkyl and cycloalkyl are as defined herein, for example, cyclopropylmethyl, cyclopropylethyl, cyclopropylpropyl, cyclopropylbutyl, cyclobutylmethyl, cyclobutylethyl, cyclobutylpropyl, cyclobutylbutyl, cyclopentylmethyl, cyclopentylethyl, cyclopentylpropyl, cyclopentylbutyl, cyclohexylmethyl, cyclohexylethyl, cyclohexylpropyl, cyclohexylbutyl and the like.

The term "$C_4$-$C_{10}$ alkylcycloalkyl" means a cycloalkyl substituted with an alkyl group and contains a total of 4 to m carbon atoms, such as 4 to 10 carbon atoms, preferably 4 to 8 carbon atoms, more preferably 4 to 6 carbon atoms, wherein the alkyl and cycloalkyl are as defined herein, for example, methylcyclopropyl, ethylcyclopropyl, propylcyclopropyl, butylcyclopropyl, methylcyclobutyl, ethylcyclobutyl, propylcyclobutyl, butylcyclobutyl, methylcyclopentyl, ethylcyclopentyl, propylcyclopentyl, butylcyclopentyl, methylcyclohexyl, ethylcyclohexyl, propylcyclohexyl, butylcyclohexyl, and the like.

As used herein, the term "$C_6$-$C_m$ aryl" refers to a monocyclic, bicyclic or tricyclic aromatic hydrocarbon group containing 6 to m carbon atoms, such as 6 to 18, preferably 6 to 10 carbon atoms. As examples of $C_6$-$C_m$ aryl groups, mention may be made of phenyl, tolyl, ethylphenyl, propylphenyl, butylphenyl, xylyl, methylethylphenyl, diethylphenyl, methylpropylphenyl, naphthyl, and the like; phenyl or naphthyl is preferred, especially phenyl (also represented as $C_6H_5$ as a substituent).

The term "$C_7$-$C_{20}$ aralkyl" means an alkyl group substituted with an aryl group and contains a total of 7 to 20 carbon atoms, such as 7 to 12, preferably 7 to 10 carbon atoms, more preferably 7 to 8 carbon atoms, wherein the alkyl and aryl groups are as defined herein, for example, benzyl, phenylethyl, naphthylmethyl, and naphthylethyl.

The term "$C_7$-$C_{20}$ alkylaryl" means an aryl group substituted with an alkyl group and contains a total of 7 to 20 carbon atoms, such as 7 to 12, preferably 7 to 10 carbon atoms, more preferably 7 to 8 carbon atoms, wherein the alkyl and aryl groups are as defined herein, for example, methylphenyl, dimethylphenyl, trimethylphenyl, ethylphenyl, diethylphenyl, triethylphenyl, methylnaphthyl, ethylnaphthyl and the like.

The terms "$C_n$-$C_m$ alkoxy" and "$C_n$-$C_m$ alkylthio" refer to a $C_n$-$C_m$ alkyl group having an oxygen atom or a sulfur atom as a linking group bonded to any carbon atom of the open-chain $C_n$-$C_m$ alkane corresponding to the $C_n$-$C_m$ alkyl group, for example, a $C_1$-$C_{20}$ alkoxy (or alkylthio) group, preferably a $C_1$-$C_{12}$ alkoxy (or alkylthio) group, more preferably a $C_1$-$C_8$ alkoxy (or alkylthio) group, and specifically preferably a $C_1$-$C_6$ alkoxy (or alkylthio) group, particularly preferably a $C_1$-$C_4$ alkoxy (or alkylthio) group. $C_1$-$C_8$ alkoxy can be methoxy, ethoxy, propoxy, isopropoxy, n-butoxy, 2-butoxy, tert-butoxy, pentyloxy, isopentyloxy, hexyloxy, heptyloxy, octyloxy, isooctyloxy, and isomers thereof. $C_1$-$C_4$ alkoxy may be methoxy, ethoxy, propoxy, isopropoxy, n-butoxy, sec-butoxy, isobutoxy, tert-butoxy, and isomers thereof. $C_1$-$C_8$ alkylthio can be methylthio, ethylthio, propylthio, isopropylthio, n-butylthio, 2-butylthio, tert-butylthio, pentylthio, isopentylthio, hexylthio, heptylthio, octylthio, isooctylthio, and isomers thereof. $C_1$-$C_4$ alkylthio can be methylthio, ethylthio, propylthio, isopropylthio, n-butylthio, and isomers thereof.

The terms "$C_2$-$C_m$ alkenyloxy" and "$C_2$-$C_m$ alkenylthio" refer to a $C_2$-$C_m$ alkenyl group having an oxygen atom or a sulfur atom as a linking group bonded to any saturated carbon atom of the $C_2$-$C_m$ alkene corresponding to the $C_2$-$C_m$ alkenyl group, for example, a $C_2$-$C_{20}$ alkenyloxy (or alkenylthio) group, preferably a $C_2$-$C_{12}$ alkenyloxy (or alkenylthio) group, more preferably a $C_2$-$C_8$ alkenyloxy (or alkenylthio) group, and specifically preferably a $C_2$-$C_6$ alkenyloxy (or alkenylthio) group, particularly preferably a $C_2$-$C_4$ alkenyloxy (or alkenylthio) group, for example, ethenyloxy, propenyloxy, isopropenyloxy, n-butenyloxy, sec-butenyloxy, isobutenyloxy, tert-butenyloxy, and isomers thereof, ethenylthio, propenylthio, isopropenylthio, n-butenylthio, and isomers thereof.

The terms "$C_2$-$C_m$ alkynyloxy" and "$C_2$-$C_m$ alkynylthio" refer to a $C_2$-$C_m$ alkynyl group having an oxygen atom or a sulfur atom as a linking group bonded to any saturated carbon atom of the $C_2$-$C_m$ alkyne corresponding to the $C_2$-$C_m$ alkynyl group, for example, a $C_2$-$C_{20}$ alkynyloxy (or alkynylthio) group, preferably a $C_2$-$C_{12}$ alkynyloxy (or alkynylthio) group, more preferably a $C_2$-$C_8$ alkynyloxy (or alkynylthio) group, and particularly preferably a $C_2$-$C_6$ alkynyloxy (or alkynylthio) group, especially preferably a $C_2$-$C_4$ alkynyloxy (or alkynylthio) group, for example, ethynyloxy, propynyloxy, n-butynyloxy, sec-butynyloxy, and isomers thereof, ethynylthio, propynylthio, propynylthio, n-butynylthio, sec-butynylthio, and isomers thereof.

The terms "$C_3$-$C_m$ cycloalkoxy" and "$C_3$-$C_m$ cycloalkylthio" refer to a $C_3$-$C_m$ cycloalkyl group having an oxygen atom or a sulfur atom as a linking group bonded to any ring carbon atom of the $C_3$-$C_m$ cycloalkane corresponding to the $C_3$-$C_m$ cycloalkyl group, for example, $C_3$-$C_{20}$ cycloalkoxy (or cycloalkylthio) group, preferably $C_3$-$C_8$ cycloalkoxy (or cycloalkylthio) group, more preferably $C_5$-$C_6$ cycloalkoxy (or cycloalkylthio) group, for example, cyclopropyloxy, cyclobutyloxy, cyclopentyloxy, cyclohexyloxy, cycloheptyloxy, cyclooctyloxy, cyclodecyloxy, and isomers thereof, cyclopropylthio, cyclobutylthio, cyclopentylthio, cyclohexylthio, cycloheptylthio, cyclooctylthio, cyclodecylthio, and isomers thereof.

The terms "$C_4$-$C_m$ cycloalkylalkoxy" and "$C_4$-$C_m$ cycloalkylalkylthio" refer to an alkoxy (alkylthio) group substituted with a cycloalkyl group and contain a total of 4 to m carbon atoms, such as 4 to 20 carbon atoms, preferably 4 to 8 carbon atoms, wherein the cycloalkyl and alkoxy (alkylthio) groups are as defined herein, for example, cyclopropylmethoxy, cyclopropylethoxy, cyclopropylpropoxy, cyclopropylbutoxy, cyclobutylmethoxy, cyclobutylethoxy, cyclobutylpropoxy, cyclobutylbutyloxy, cyclopentylmethoxy, cyclopentylethoxy, cyclopentylpropoxy, cyclopentylbutyoxy, cyclohexylmethoxy, cyclohexylethoxy, cyclohexylpropoxy, cyclohexylbutoxy, cyclopropylmethylthio, cyclopropylethylthio, cyclopropylpropylthio, cyclopropylbutylthio, cyclobutylmethylthio, cyclobutylethylthio, cyclobutylpropylthio, cyclobutylbutylthio, cyclopentylmethylthio, cyclopentylethylthio, cyclopentylpropylthio, cyclopentylbutylthio, cyclohexylmethylthio, cyclohexylethylthio, cyclohexylpropylthio, cyclohexylbutylthio, and the like.

The terms "$C_6$-$C_m$ aryloxy" and "$C_6$-$C_m$ arylthio" refer to a $C_6$-$C_m$ aryl group having an oxygen atom or a sulfur atom as a linking group bonded to any aromatic carbon atom of the $C_6$-$C_m$ aromatic hydrocarbon corresponding to the $C_6$-$C_m$ aryl group, for example, phenylthio, phenoxy, tolyloxy, tolylthio, naphthylthio, naphthyloxy, and the like.

In the present invention, n is 0 or 1. When n is 0, the compound of formula (I) is referred to as a coumarin oxime ester compound; when n is 1, the compound of formula (I) is referred to as a coumarin ketooxime ester compound. These two compounds are collectively referred to as coumarin (keto) oxime ester compounds.

In the present invention, $R_1$, $R_2$, $R_3$, $R_4$, and $R_5$ are independently selected from hydrogen, halogen, nitro, hydroxy, mercapto, carboxyl, $C_1$-$C_8$ carboxylate ester group, sulfonic acid group, amino, cyano, $C_1$-$C_{20}$ alkyl, $C_2$-$C_{20}$ alkenyl, $C_2$-$C_{20}$ alkynyl, $C_3$-$C_{20}$ cycloalkyl, $C_4$-$C_{20}$ cycloalkylalkyl, $C_1$-$C_{20}$ alkoxy, $C_2$-$C_{20}$ alkenyloxy, $C_2$-$C_{20}$ alkynyloxy, $C_3$-$C_{20}$ cycloalkoxy, $C_4$-$C_{20}$ cycloalkylalkoxy, $C_1$-$C_{20}$ alkylthio, $C_2$-$C_{20}$ alkenylthio, $C_2$-$C_{20}$ alkynylthio, $C_3$-$C_{20}$ cycloalkylthio, $C_4$-$C_{20}$ cycloalkylalkylthio, $C_6$-$C_{18}$ aryl, $C_6$-$C_{18}$ aryloxy and $C_6$-$C_{18}$ arylthio, wherein the aforementioned amino, $C_1$-$C_{20}$ alkyl, $C_2$-$C_{20}$ alkenyl, $C_2$-$C_{20}$ alkynyl, $C_3$-$C_{20}$ cycloalkyl, $C_4$-$C_{20}$ cycloalkylalkyl, $C_1$-$C_{20}$ alkoxy, $C_2$-$C_{20}$ alkenyloxy, $C_2$-$C_{20}$ alkynyloxy, $C_3$-$C_{20}$ cycloalkoxy, $C_4$-$C_{20}$ cycloalkylalkoxy, $C_1$-$C_{20}$ alkylthio, $C_2$-$C_{20}$ alkenylthio, $C_2$-$C_{20}$ alkynylthio, $C_3$-$C_{20}$ cycloalkylthio, $C_4$-$C_{20}$ cycloalkylalkylthio, $C_6$-$C_{18}$ aryl, $C_6$-$C_{18}$ aryloxy and $C_6$-$C_{18}$ arylthio may be optionally substituted with one or more groups independently selected from the group consisting of: halogen, nitro, hydroxy, mercapto, carboxyl, sulfonic acid group, amino, cyano, $C_1$-$C_6$ alkyl, $C_1$-$C_6$ alkoxy, $C_1$-$C_6$ alkylthio, $C_2$-$C_6$ alkenyl and $C_2$-$C_6$ alkynyl. Alternatively, $R_1$ together with $R_2$, $R_2$ together with $R_3$, $R_3$ together with $R_4$, or $R_1$ together with $R_2$ and $R_3$ together with $R_4$ form a saturated or unsaturated divalent group having 3 to 4 atoms selected from C, N, O, and S and wherein at least one of the atoms is carbon atom; and Preferably, $R_1$, $R_2$, $R_3$, $R_4$, and $R_5$ are independently selected from hydrogen, halogen, nitro, hydroxy, mercapto, carboxyl, $C_1$-$C_6$ carboxylate ester group, sulfonic acid group, amino, cyano, $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkylalkyl, $C_1$-$C_6$ alkoxy, $C_2$-$C_6$ alkenyloxy, $C_2$-$C_6$ alkynyloxy, $C_3$-$C_8$ cycloalkoxy, $C_4$-$C_8$ cycloalkylalkoxy, $C_1$-$C_6$ alkylthio, $C_2$-$C_6$ alkenylthio, $C_2$-$C_6$ alkynylthio, $C_3$-$C_8$ cycloalkylthio, $C_4$-$C_8$ cycloalkylalkylthio, $C_6$-$C_{10}$ aryl, $C_6$-$C_{10}$ aryloxy and $C_6$-$C_{10}$ arylthio, wherein the aforementioned amino, $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkylalkyl, $C_1$-$C_6$ alkoxy, $C_2$-$C_6$ alkenyloxy, $C_2$-$C_6$ alkynyloxy, $C_3$-$C_8$ cycloalkoxy, $C_4$-$C_8$ cycloalkylalkoxy, $C_1$-$C_6$ alkylthio, $C_2$-$C_6$ alkenylthio, $C_2$-$C_6$ alkynylthio, $C_3$-$C_8$ cycloalkylthio, $C_4$-$C_8$ cycloalkylalkylthio, $C_6$-$C_{10}$ aryl, $C_6$-$C_{10}$ aryloxy and $C_6$-$C_{10}$ arylthio may be optionally substituted with one or more groups independently selected from the group consisting of halogen, nitro, hydroxy, mercapto, carboxyl, sulfonic acid group, amino, cyano, $C_1$-$C_4$ alkyl, $C_1$-$C_4$ alkoxy, $C_1$-$C_4$ alkylthio, $C_2$-$C_4$ alkenyl and $C_2$-$C_4$ alkynyl. Alternatively, $R_1$ together with $R_2$, $R_2$ together with $R_3$, or $R_3$ together with $R_4$ form a saturated or unsaturated divalent group having 3 to 4 atoms selected from C, N, O, and S and wherein at least one of the atoms is carbon atom.

Particularly preferably, $R_1$, $R_2$, $R_3$, $R_4$, and $R_5$ are independently selected from hydrogen, halogen, nitro, $C_1$-$C_4$ carboxylate ester group, $C_1$-$C_4$ alkyl, $C_2$-$C_4$ alkenyl, $C_1$-$C_4$ alkoxy, $C_1$-$C_4$ alkylthio, mono($C_1$-$C_4$ alkyl)amino, di($C_1$-$C_4$ alkyl)amino, phenoxy and phenylthio. Alternatively, $R_1$ together with $R_2$, $R_2$ together with $R_3$, or $R_3$ together with $R_4$ form a saturated or unsaturated divalent group having 3 to 4 atoms selected from C, N, O, and S and wherein at least one of the atoms is carbon atom, for example, —O—$CH_2$—O—, —S—$CH_2$—S—, —N—$CH_2$—N—, —O—$CH_2CH_2$—O—, —S—$CH_2CH_2$—S—, —N—$CH_2CH_2$—N— or —CH=CH—CN=CH—.

In the present invention, $R_6$ and $R_7$ independently represent linear or branched $C_1$-$C_{20}$ alkyl, $C_3$-$C_{10}$ cycloalkyl, $C_4$-$C_{10}$ cycloalkylalkyl, $C_4$-$C_{10}$ alkylcycloalkyl, $C_6$-$C_{20}$ aryl, $C_7$-$C_{20}$ aralkyl and $C_7$-$C_{20}$ alkylaryl, wherein the aforementioned $C_1$-$C_{20}$ alkyl, $C_3$-$C_{10}$ cycloalkyl, $C_4$-$C_{10}$ cycloalkylalkyl, $C_4$-$C_{10}$ alkylcycloalkyl, $C_6$-$C_{20}$ aryl, $C_7$-$C_{20}$ aralkyl and $C_7$-$C_{20}$ alkylaryl are optionally substituted with one or more groups independently selected from the group consisting of: $C_1$-$C_6$ alkylthio, $C_1$-$C_6$ alkoxy, $C_1$-$C_6$ alkyl, halogen, nitro, amino, mono($C_1$-$C_6$ alkyl)amino, di($C_1$-$C_6$ alkyl) amino and mercapto.

Preferably, $R_6$ and $R_7$ independently represent linear or branched $C_1$-$C_8$ alkyl, $C_3$-$C_8$ cycloalkyl, $C_4$-$C_8$ cycloalkylalkyl, $C_4$-$C_8$ alkylcycloalkyl, $C_6$-$C_{10}$ aryl, $C_7$-$C_1$ aralkyl and $C_7$-$C_{11}$ alkylaryl, wherein the aforementioned $C_1$-$C_8$ alkyl, $C_3$-$C_8$ cycloalkyl, $C_4$-$C_8$ cycloalkylalkyl, $C_4$-$C_8$ alkylcycloalkyl, $C_6$-$C_{10}$ aryl, $C_7$-$C_{11}$ aralkyl and $C_7$-$C_{11}$ alkylaryl may be optionally substituted with one or more groups independently selected from the group consisting of: $C_1$-$C_4$ alkyl, $C_1$-$C_4$ alkylthio, $C_1$-$C_4$ alkoxy, halogen, nitro, amino, mono($C_1$-$C_4$ alkyl)amino, di($C_1$-$C_4$ alkyl)amino and mercapto.

Particularly preferably, $R_6$ and $R_7$ are independently selected from linear or branched $C_1$-$C_8$ alkyl, $C_5$-$C_6$ cycloalkyl, $C_1$-$C_4$ alkyl substituted with $C_5$-$C_6$ cycloalkyl, $C_1$-$C_4$ alkyl substituted with phenyl, and phenyl, wherein the aforementioned phenyl each may be optionally substituted with one or more groups independently selected from the group consisting of: $C_1$-$C_4$ alkyl, $C_1$-$C_4$ alkylthio, $C_1$-$C_4$ alkoxy, halogen, nitro, amino, mono($C_1$-$C_4$ alkyl)amino, di($C_1$-$C_4$ alkyl)amino and mercapto. Especially, $R_6$ is linear or branched $C_1$-$C_6$ alkyl, $C_5$-$C_6$ cycloalkyl, $C_1$-$C_2$ alkyl substituted with $C_5$-$C_6$ cycloalkyl, or phenyl, and the aforementioned phenyl is optionally substituted with one or more groups independently selected from the group consisting of: $C_1$-$C_4$ alkyl, halogen, nitro, amino and mercapto, and $R_7$ is linear or branched $C_1$-$C_7$ alkyl or phenyl, wherein the phenyl is optionally substituted with one or more groups independently selected from the group consisting of $C_1$-$C_4$ alkyl, $C_1$-$C_4$ alkylthio, $C_1$-$C_4$ alkoxy, halogen, nitro, amino, mono ($C_1$-$C_4$ alkyl)amino, di($C_1$-$C_4$ alkyl)amino and mercapto.

Also preferably, $R_5$ is H.

Especially preferably, when n is 0, $R_1$, $R_2$, $R_3$, and $R_4$ are independently selected from hydrogen, halogen, nitro, $C_1$-$C_4$ carboxylate ester group, $C_1$-$C_6$ alkyl, $C_2$-$C_4$ alkenyl, $C_1$-$C_4$ alkoxy, $C_1$-$C_4$ alkylthio, mono($C_1$-$C_4$ alkyl)amino, di($C_1$-$C_4$ alkyl)amino, phenoxy and phenylthio; or, $R_1$ together with $R_2$, $R_2$ together with $R_3$, or $R_3$ together with $R_4$ form a saturated or unsaturated divalent group having 3 to 4 atoms selected from C, N, O, and S and wherein at least one of the atoms is carbon atom, for example, —CH=CH—CN=CH—;

$R_6$ is linear or branched $C_1$-$C_6$ alkyl, halo $C_1$-$C_6$ alkyl, $C_5$-$C_6$ cycloalkyl, $C_1$-$C_2$ alkyl substituted with $C_5$-$C_6$ cycloalkyl, or phenyl, and the aforementioned phenyl is optionally substituted with one or more groups independently selected from the group consisting of: fluorine, chlorine, bromine, $C_1$-$C_4$ alkyl, $C_1$-$C_4$ alkoxy, $C_1$-$C_4$ alkylthio and halo $C_1$-$C_4$ alkyl, and $R_7$ is linear or branched $C_1$-$C_7$ alkyl or phenyl, wherein the phenyl is optionally substituted with one or more groups independently selected from the group consisting of: $C_1$-$C_4$ alkyl, halogen, nitro, amino, mono($C_1$-$C_4$ alkyl)amino and di($C_1$-$C_4$ alkyl)amino, or when n is 1, $R_1$, $R_2$, $R_3$, and $R_4$ are independently selected from hydrogen, $C_1$-$C_4$ alkyl, $C_1$-$C_4$ alkoxy, $C_1$-$C_4$ alkylthio, mono ($C_1$-$C_4$ alkyl)amino, di($C_1$-$C_4$ alkyl)amino, phenoxy and phenylthio; or, $R_1$ together with $R_2$, $R_2$ together with $R_3$, or $R_3$ together with $R_4$ form a saturated or unsaturated divalent group having 3 to 4 atoms selected from C, N, O, and S and wherein at least one of the atoms is carbon atom, for example, —O—$CH_2$—O—, —S—$CH_2$—S—, —N—$CH_2$—N—, —O—$CH_2CH_2$—O—, —S—$CH_2CH_2$—S— or —N—$CH_2CH_2$—N;

$R_6$ is linear or branched $C_1$-$C_6$ alkyl, halo $C_1$-$C_6$ alkyl, $C_5$-$C_6$ cycloalkyl or $C_1$-$C_2$ alkyl substituted with $C_5$-$C_6$ cycloalkyl, and $R_7$ is linear or branched $C_1$-$C_6$ alkyl or phenyl optionally substituted with nitro.

In a particularly preferred embodiment of the present invention, the compound of formula (I) is selected from compounds 1 to 50. The compounds 1 to 50 were prepared in Examples 1 to 50, respectively.

According to a second aspect of the present invention, a method for preparing a compound of formula (I) of the present invention is provided, comprising the following steps:

(1) oximation reaction: when n is 0, a compound of formula (II) is subjected to oximation reaction with hydroxylamine and/or hydroxylamine hydrochloride to obtain a compound of formula (IIIa)

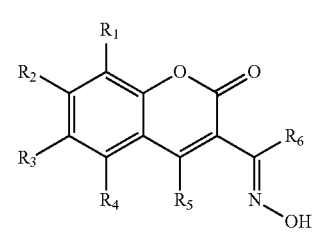

(II)

when n is 1, a compound of formula (II) is subjected to oximation reaction with a reagent selected from the group consisting of nitrous acid, nitrite and alkyl nitrite to obtain a compound of formula (IIIb):

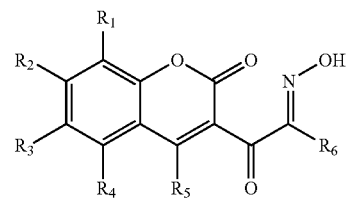

(IIIa)

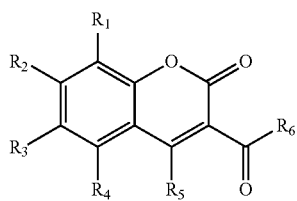

(IIIb)

wherein $R_1$-$R_5$ and $R_6$ in formulae (II), (IIIa) and (IIIb) are as defined for formula (I); and (2) the compound of formula (IIIa) or (IIIb) is esterified to obtain the compound of formula (I).

In order to prepare the compound of formula (I) of the present invention, it is necessary to first perform an oximation reaction to introduce an oxime group, and then the hydroxyl group in the oxime group is converted into the corresponding ester group through an esterification reaction, thereby obtaining the coumarin (keto) oxime ester compound of the present invention.

Oximation Reaction

The oximation reaction usually starts with a carbonyl compound. For this reason, when n is 0, a compound of formula (II) is subjected to oximation reaction with hydroxylamine and/or hydroxylamine hydrochloride to obtain a compound of formula (IIIa)

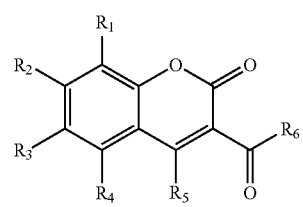

(II)

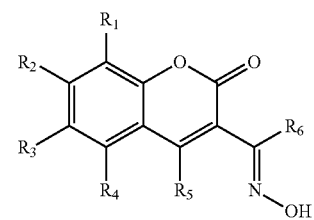

(IIIa)

$R_1$-$R_5$ and $R_6$ in formulae (II) and (IIIa) are as defined for formula (I). In order to convert the acyclic carbonyl group in the formula (II) to an oxime group, it is generally necessary to use hydroxylamine hydrochloride ($NH_2OH \cdot HCl$), hydroxylamine ($NH_2OH$) or a mixture thereof as the oximating agent. The oximation reaction is usually carried out in an organic solvent, preferably in an organic polar solvent. The solvent that can be used are, for example, ethanol or aqueous ethanol. In order to promote the completion of the oximation reaction, bases such as sodium acetate, pyridine, piperidine, triethylamine are generally added. Among them, pyridine, piperidine, and triethylamine can also be used as bases and/or solvents or co-solvents. The temperature of oximation reaction is generally the reflux temperature of the solvent, and the temperature range is usually 60 to 120° C. The time of oximation reaction is not particularly limited either, but it is usually carried out for 0.1 to 20 hours, preferably 0.5 to 10 hours. The relative amount of the compound of formula (II) and the compound selected from hydroxylamine and/or hydroxylamine hydrochloride is not particularly limited. Generally, they are used in approximately equimolar amounts, for example, the molar ratio of the two is 1:1.5 to 1.5:1, preferably 1:1.2 to 1.2:1.

When n is 1, the compound of formula (II) is subjected to oximation reaction with nitrous acid, nitrite and/or alkyl nitrite to obtain a compound of formula (IIIb):

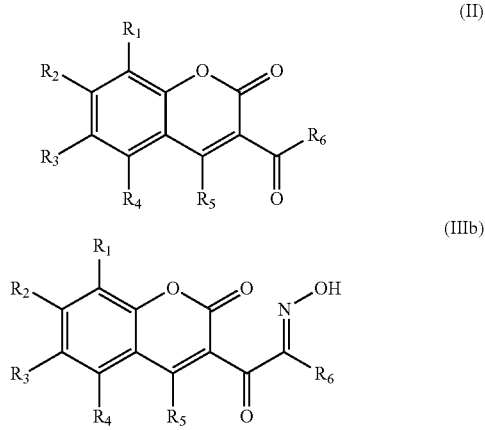

wherein, $R_1$ to $R_5$ and $R_6$ in formulae (II) and (IIIb) are as defined for formula (I). In order to convert the acyclic carbonyl group in formula (II) to a ketoxime group, it is generally necessary to use nitrous acid, nitrite and/or alkyl nitrite as the oximating agent. This reagent nitrosates the "active" methyl/methylene (α-methyl/methylene, that is, the methyl/methylene next to the acyclic carbonyl group). As the nitrite, sodium nitrite is usually used. The alkyl nitrite may be a $C_1$-$C_6$ alkyl nitrite such as methyl nitrite, ethyl nitrite, isopropyl nitrite, butyl nitrite, isoamyl nitrite. The oximation reaction is usually carried out in an organic solvent, preferably in an organic polar solvent. Solvents that can be used are, for example, ethanol or aqueous ethanol. In order to promote the oximation reaction to completion, it is generally necessary to add concentrated hydrochloric acid. Concentrated hydrochloric acid may also be used as the acid and/or solvent or co-solvent. The temperature of oximation reaction is low, and the temperature range is usually −30 to 20° C., preferably 5 to 20° C. The time of oximation reaction is not particularly limited either, it is usually carried out for 0.1 to 20 hours, preferably 0.5 to 10 hours. The relative amount of the compound of formula (II) and the compound selected from the group consisting of nitrous acid, nitrite and/or alkyl nitrite is not particularly limited. Generally, they are used in approximately equimolar amounts, for example, the molar ratio of the two is 1:1.5 to 1.5:1, preferably 1:1.2 to 1.2:1.

There may be two configurations for each oxime ester group, either (Z) or (E). Isomers can be separated by conventional methods, but it is also possible to use a mixture of isomers as the photo-initiated substance. The present invention therefore also relates to a mixture of configurational isomers of a compound of formula (I).

Esterification Reaction

Esterification of the compounds of the formulae (IIIa) and (IIIb) is conventional, and by this reaction, the hydroxyl group in the oxime group is converted to an ester group, thereby obtaining the compound of the formula (I). As the esterifying agent, it is not particularly limited as long as the hydroxyl group in the oxime group of the compounds of the formulae (IIIa) and (IIIb) can be converted into an ester group. As the esterifying agent, a corresponding acid halide, such as an acid chloride, a corresponding carboxylic acid, or a corresponding anhydride can be used. These compounds can be represented by formulae (IVa), (IVb) and (IVc), respectively:

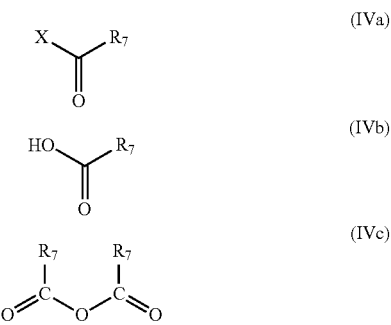

wherein X is halogen, especially chlorine, and $R_7$ is as defined for formula (I).

In order to accelerate the esterification reaction, the above-mentioned esterification reaction is usually performed in the presence of a catalyst suitable for the esterification reaction. As the catalyst, either an acidic catalyst or a basic catalyst can be used. As the catalyst, one or more selected from the group consisting of sulfuric acid, perchloric acid, zinc chloride, ferric chloride, pyridine, p-toluenesulfonic acid, sodium hydroxide, potassium hydroxide, sodium carbonate, sodium bicarbonate, sodium tert-butoxide, sodium ethoxide, sodium hydride, potassium hydride, calcium hydride and tertiary amines, for example, trialkylamines, such as trimethylamine and triethylamine can be used. The amount of catalyst used is conventional and can be determined by common knowledge in the art, or by several routine preliminary experiments.

In order to increase the yield of the compound of formula (I), it is advantageous to remove the water produced by the esterification reaction during the esterification reaction. This can be done, for example, by distillation condensation.

The above-mentioned esterification reaction is usually performed in a solvent, preferably in an organic solvent. The choice of the type of the solvent is not particularly limited, as long as it can dissolve the compound of formula (IIIa) or formula MN and the esterifying agent and is chemically inert to the esterification reaction, that is, it does not participate in the esterification reaction. As examples of the solvent, mention may be made of tetrahydrofuran, benzene, toluene, N,N-dimethylformamide, dichloromethane and acetone. A single solvent may be used, or a mixture of two or more solvents may be used.

The relative amount of the compound of formula (IIIa) or formula (IIIb) and the esterifying agent selected from the compounds of (IVa), (IVb) and (IVc) is not particularly limited. Generally, they are used in approximately equimolar amounts, for example, the molar ratio of the two is 1:1.5 to 1.5:1, preferably 1:1.2 to 1.2:1.

The esterification reaction can be carried out over a very wide temperature range. According to the present invention, it is advantageous that the esterification reaction is carried out at a temperature of −10° C. to 150° C., preferably 0° C. to 100° C., preferably at room temperature. The time of esterification reaction is not particularly limited either, but the esterification reaction is usually carried out for 1 to 24 hours, preferably 1 to 12 hours.

After the completion of the esterification reaction, a reaction mixture comprising a compound of formula (I) is obtained. Therefore, the reaction mixture needs to be worked up to obtain a purified compound of formula (I). Generally, the reaction mixture obtained by the esterification reaction is first filtered, and the filtrate portion is taken out. Then, the filtrate is washed to remove the catalyst and unreacted raw materials. The washing liquid is not particularly limited as long as it can remove the catalyst and unreacted raw materials. As examples of the washing liquid, dilute hydrochloric acid (aqueous solution), saturated aqueous sodium bicarbonate solution and water can be mentioned. The concentration of dilute hydrochloric acid is not particularly limited. Generally, dilute hydrochloric acid having a concentration of 5 to 12% is used. Washing with a washing liquid can be performed once or multiple times; in the case of multiple times, a single washing liquid can be used, or different washing liquids can be used sequentially. According to the present invention, it is advantageous that the filtrate obtained by filtering the reaction mixture obtained from the esterification reaction is washed sequentially with dilute hydrochloric acid, saturated aqueous sodium bicarbonate solution and water. Certainly, after each washing with the washing liquid, the aqueous phase needs to be discarded before the organic phase is washed with the next washing liquid. After washing, drying is required to remove residual water. For this purpose, anhydrous sodium sulfate can usually be used for drying. After drying, the residual organic solvent is removed. The means for removing the organic solvent is not particularly limited, and the organic solvent can usually be removed by distillation under reduced pressure. After removal of the residual organic solvent, a crude product of the compound of formula (I) is obtained. If it is desired to further improve the purity of the compound of formula (I), the compound can be further purified, for example, by means of recrystallization. The choice of the recrystallization solvent is conventional and is not particularly limited. According to the present invention, it is advantageous to recrystallize the crude product of the compound of formula (I) with methanol.

The compound of formula (I) of the present invention has a large conjugated system and a long absorption wavelength, and has a strong absorption in the wavelength range of 300 to 450 nm, particularly 350 to 420 nm, especially 365 to 405 nm, so it can be applied to UV-LED light curing system. The raw materials for preparing the compound of the formula (I) of the present invention are all coumarin ketone compounds with little toxicity, and the harm degree to human body and environment is reduced compared with the traditional photoinitiator.

Therefore, according to a third aspect of the present invention, use of the compound of formula (I) according to the present invention as a photoinitiator is provided. The compound of formula (I) of the present invention can effectively initiate a curing reaction as a photoinitiator in a UV-LED light curing system.

The compound of formula (I) can be used as a photoinitiator or photosensitizer in the fields of coatings, inks, microelectronics, printing and the like. When the compound of formula (I) is used as a photoinitiator or photosensitizer, its amount is conventional or can be determined through routine preliminary tests.

EXAMPLES

The present invention will be further described below with reference to specific examples, but it should not be construed as limiting the scope of the present invention.

Example 1: Preparation of Compound 1

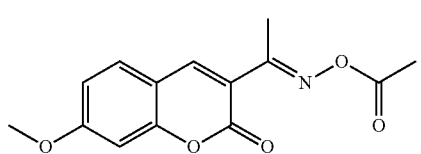

The synthetic route of compound 1 is as follows:

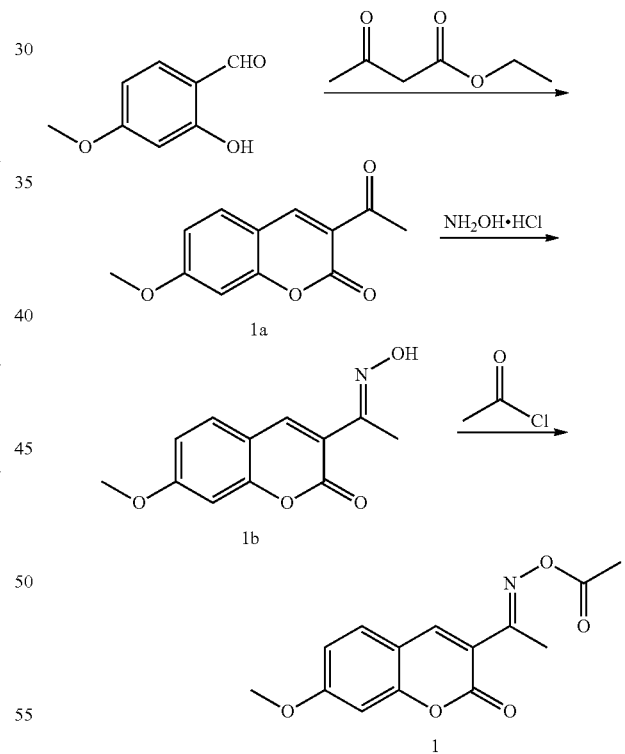

Synthesis of Intermediate 1a 4-methoxysalicylic aldehyde (0.0293 mol, 4.45 g) was added to a 50 mL three-necked round bottom flask containing 15 mL of ethanol. After stirring well, the mixture was heated to 35° C. to dissolve all the reactants in ethanol. Then hexahydropyridine (0.01 mol, 1 mL) and ethyl acetoacetate (0.036 mol, 4.68 g) were added, and the reaction mixture was heated to reflux, and the reaction was carried out for 1 hour under stirring. After the reaction was completed, the mixture was cooled to room temperature, filtered to obtain a yellow solid, which was then recrystallized with ethanol to obtain 6.2 g of the product with a yield of 97%, which was identified as compound 1a. 1H-NMR (400 MHz, CDCl$_3$) δ 2.70 (s, 3H), 3.91 (s, 3H), 6.82 (d, 1H), 6.88 (d, 1H), 7.55 (d, 1H), 8.48 (s, 1H).

Synthesis of Intermediate 1b

The intermediate product 1a (4.66 g, 0.021 mol) and 50 mL of a mixed solution of ethanol and water (V$_{ethanol}$:V$_{water}$=2:1) were poured into a 100 mL three-necked round bottom flask, and then hydroxylamine hydrochloride (1.45 g, 0.021 mol) and sodium acetate (1.72 g, 0.021 mol) were added. After reacting under stirring at 70° C. for 0.5 hours, the reaction solution was filtered, and then the filtrate was subjected to vacuum rotary evaporation to obtain a pale yellow solid, which was recrystallized with ethanol to obtain 4.47 g a product with a yield of 90%, which was identified as compound 1b. 1H-NMR (400 MHz, DMSO-D6) δ 2.05 (s, 3H), 3.86 (s, 3H), 6.95 (d, 1H), 7.01 (d, 1H), 7.70 (d, 1H), 8.03 (s, 1H), 11.30 (s, 1H).

Synthesis of Target Product 1

The above intermediate 1b (2.08 g, 0.009 mol) and 30 ml of tetrahydrofuran were added to a 100 mL three-neck round bottom flask, then acetyl chloride (0.78 g, 0.01 mol) and triethylamine (1.35 g, 0.013 mol) were added, and the reaction was carried out at room temperature and under stirring for 1 hour. The reaction was terminated. After the reaction solution was filtered, the filtrate was poured into water and extracted with ethyl acetate. The organic phase was collected, washed sequentially with dilute hydrochloric acid solution, saturated sodium carbonate solution, and distilled water, and then the organic phase was collected and dried with MgSO$_4$ overnight. After filtration, the organic phase was distilled off under reduced pressure to obtain 2.37 g a white solid with a yield of 97.0%, which was identified as Compound 1. 1H-NMR (400 MHz, CDCl$_3$) δ 2.25 (s, 3H), 2.40 (s, 3H), 3.89 (s, 3H), 6.82 (d, 1H), 6.87 (d, 1H), 7.44 (d, 1H), 8.04 (s, 1H).

Examples 2 to 20

The method of Example 1 was repeated, the reaction raw materials were appropriately changed, and the compounds 2 to 20 and their NMR data in the following table were obtained.

| Example | Compounds | H-NMR δ (ppm) |
|---|---|---|
| 2 | *(structure 2)* | δ 1.04 (d, 6H), 1.76 (m, 1H), 3.06 (s, 6H), 3.83 (s, 3H), 6.471-6.477 (d, 1H), 6.58-6.61 (d, 1H), 7.30-7.32 (d, 1H), 7.98 (s, 1H), 7.66 (m, 2H), 8.21 (m, 2H) |
| 3 | *(structure 3)* | δ 1.20-1.24 (t, 6H), 2.23 (s, 3H), 2.39 (s, 3H), 3.40-3.45 (q, 4H), 6.471-6.477 (d, 1H), 6.58-6.61 (d, 1H), 7.30-7.32 (d, 1H), 7.98 (s, 1H) |
| 4 | *(structure 4)* | δ 1.20-1.24 (t, 6H), 2.39 (s, 3H), 3.40-3.45 (q, 4H), 6.471-6.477 (d, 1H), 6.58-6.61 (d, 1H), 7.30-7.32 (d, 1H), 7.98 (s, 1H), 7.79 (m, 1H) 7.66 (m, 2H), 8.21 (m, 2H) |

-continued

| Example | Compounds | H-NMR δ (ppm) |
|---|---|---|
| 5 | *structure 5* | δ 1.20-1.24 (t, 6H), 2.23 (s, 3H), 2.52 (s, 3H), 3.40-3.45 (q, 4H), 6.471-6.477 (d, 1H), 6.58-6.61 (d, 1H), 7.30-7.32 (d, 1H), 7.98 (s, 1H), 7.66 (m, 2H), 8.21 (m, 2H) |
| 6 | *structure 6* | δ 0.88 (t, 3H), 1.31 (m, 2H), 1.29 (m, 6H), 1.52 (m, 2H), 2.30 (t, 2H), 1.20-1.24 (t, 6H), 2.39 (s, 3H), 3.40-3.45 (q, 4H), 6.471-6.477 (d, 1H), 6.58-6.61 (d, 1H), 7.30-7.32 (d, 1H), 7.98 (s, 1H) |
| 7 | *structure 7* | δ 2.25 (s, 3H), 3.89 (s, 3H), 6.82 (d, 1H), 7.44 (d, 1H), 8.04 (s, 1H), 7.79 (m, 1H) 7.66 (m, 2H), 8.21 (m, 2H) |
| 8 | *structure 8* | δ 0.88 (t, 3H), 1.52 (m, 2H), 2.30 (t, 2H), 2.53 (s, 3H), 3.11 (s, 3H), 7.74 (d, 1H), 7.34 (d, 1H), 7.32 (s, 1H) 7.54 (s, 1H) |
| 9 | *structure 9* | δ 1.20-1.24 (t, 6H), 2.39 (s, 3H), , 6.471-6.477 (d, 1H), 6.58-6.61 (d, 1H), 7.30-7.32 (d, 1H), 7.98 (s, 1H), 7.79 (m, 1H) 7.66 (m, 2H), 8.21 (m, 2H) |
| 10 | *structure 10* | δ 2.23 (s, 3H), 2.39 (s, 3H), 6.471-6.477 (d, 1H), 6.58-6.61 (d, 1H), 7.30-7.32 (d, 1H), 7.98 (s, 1H) |

-continued
| Example | Compounds | H-NMR δ (ppm) |
|---|---|---|
| 11 | 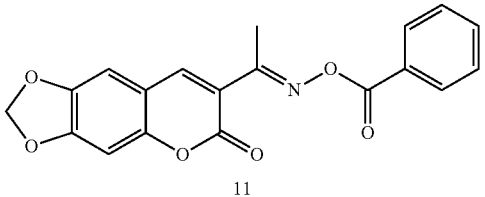 [SMILES: C/C(=N\OC(=O)c1ccccc1)c1cc2cc3c(cc2oc1=O)OCO3]<br>11 | δ 2.39 (s, 3H), 6.471 (s, 1H), 6.58 (s, 1H), 7.30 (s, 1H), 7.98 (s, 1H), 7.66 (m, 2H), 8.21 (m, 2H) |
| 12 | 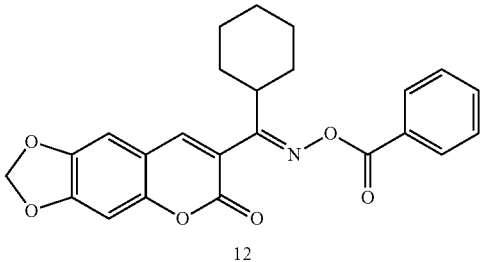 [SMILES: O=C(O/N=C(/c1cc2cc3c(cc2oc1=O)OCO3)C1CCCCC1)c1ccccc1]<br>12 | δ 1.43-1.75 (m, 10), 2.42 (m, 1H), 6.471 (s, 1H), 6.58 (s, 1H), 7.30 (s, 1H), 7.98 (s, 1H), 7.66 (m, 2H), 8.21 (m, 2H) |
| 13 | 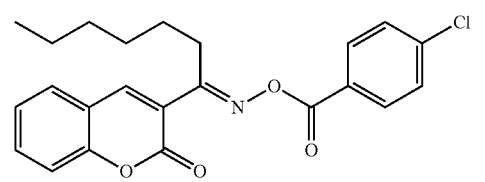<br>13 | δ 0.90 (t, 3H), 1.31 (m, 2H), 1.29 (m, 4H), 1.47 (m, 2H) 1.53 (t, 2H), 7.42 (d, 2H), 7.65 (m, 1H), 7.84 (s, 1H), 7.54 (s, 1H), 7.66 (m, 2H), , 8.21 (m, 2H) |
| 14 | 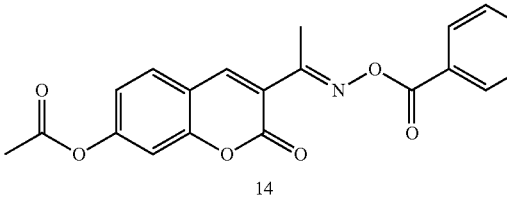<br>14 | δ 1.20 (s, 3H), 2.39 (s, 3H), , 6.471-6.477 (d, 1H), 6.58-6.61 (d, 1H), 7.30-7.32 (d, 1H), 7.98 (s, 1H), 7.79 (m, 1H) 7.66 (m, 2H), 8.21 (m, 2H) |
| 15 | 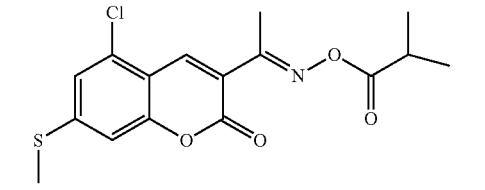<br>15 | δ 1.09 (t, 6H), 2.67 (m, 2H), 2.39 (s, 3H), 3.11 (s, 3H), 7.74 (d, 1H), 7.34 (d, 1H), 7.32 (s, 1H) |
| 16 | 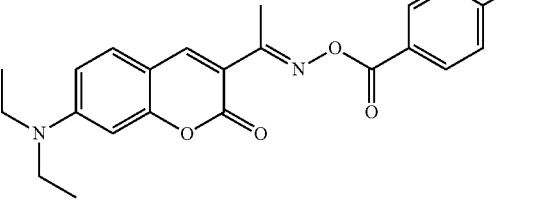<br>16 | δ 1.20-1.24 (t, 6H), 2.39 (s, 3H), 3.40-3.45 (q, 4H), 6.471-6.477 (d, 1H), 6.58-6.61 (d, 1H), 7.30-7.32 (d, 1H), 7.98 (s, 1H), 7.66 (d, 2H), 8.21 (d, 2H) |

-continued
| Example | Compounds | H-NMR δ (ppm) |
|---|---|---|
| 17 | 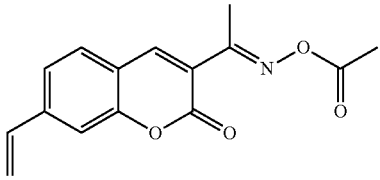<br>17 | δ 2.23 (s, 3H), 2.39 (s, 3H), 5.61 (d, 2H), 6.53 (t, 1H). 6.471 (d, 1H), 6.58 (d, 1H), 7.30 (s, 1H), 7.98 (s, 1H) |
| 18 | 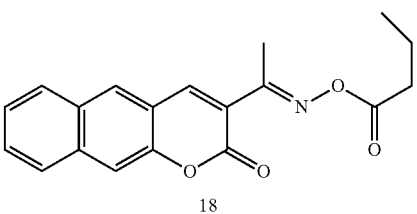 [SMILES: CCCC(=O)O/N=C(\C)c1cc2cc3ccccc3cc2oc1=O]<br>18 | δ 0.88 (t, 3H), 1.52 (m, 2H), 2.30 (t, 2H), 2.53 (s, 3H), 7.74 (d, 2H), 7.34 (d, 2H), 7.32 (s, 1H) 7.54 (s, 1H), 7.63 (s, 1H) |
| 19 | 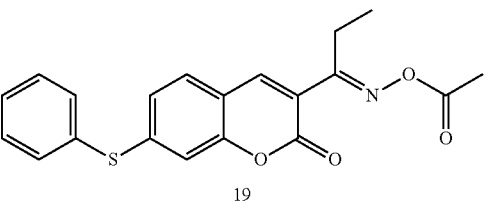 [SMILES: CC/C(=N\OC(C)=O)c1cc2ccc(Sc3ccccc3)cc2oc1=O]<br>19 | δ 1.04 (t, 3H), 1.57 (p, 2H), 2.53 (s, 3H) 6.471-6.477 (d, 1H), 6.58-6.61 (d, 1H), 7.25-7.28 (m, 2H), 7.30-7.32 (d, 1H), 7.41-7.43 (d, 2H), 7.19 (m, 1H), 7.98 (s, 1H) |
| 20 | 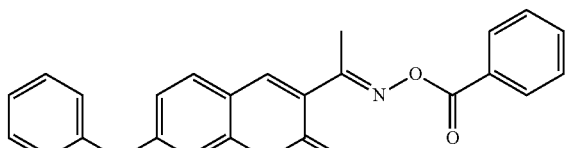<br>20 | δ 2.39 (s, 3H), 6.741-6.477 (d, 1H), 6.58-6.61 (d, 1H), 7.25-7.28 (m, 2H), 7.30-7.32 (d, 1H), 7.41-7.43 (d, 2H), 7.19 (m, 1H), 7.98 (s, 1H), 7.79 (m, 1H) 7.66 (m, 2H), 8.21 (m, 2H) |

Example 21: Preparation of Compound 21

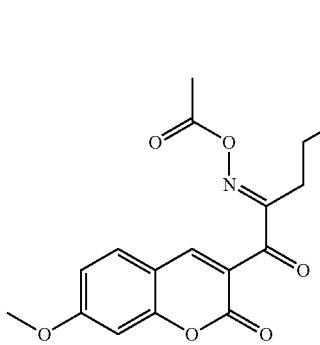

The synthetic route of compound 21 is as follows:

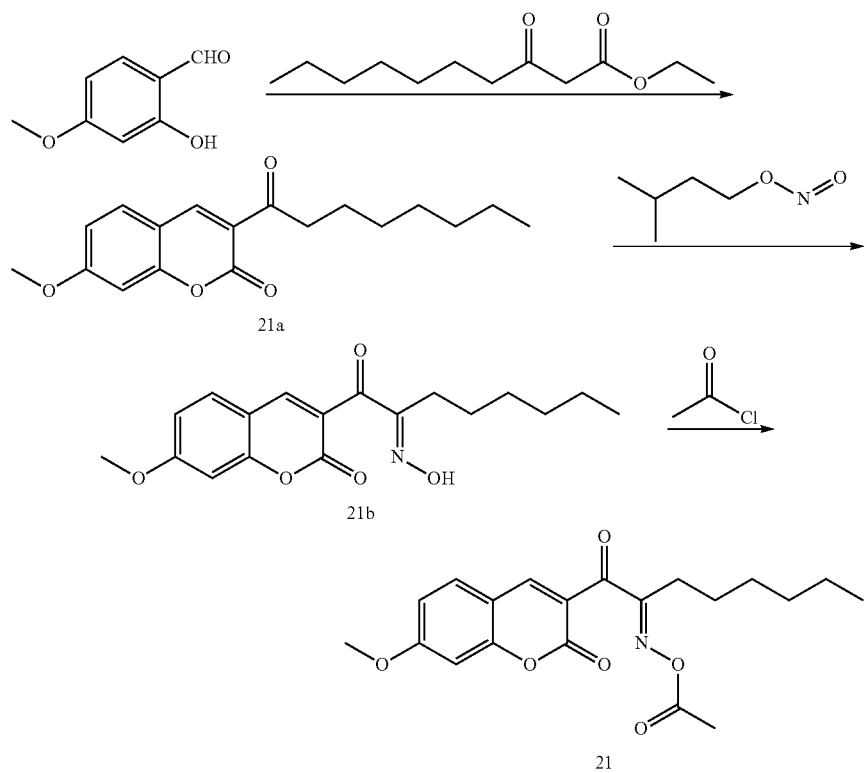

Synthesis of Intermediate 21a 4-methoxysalicylic aldehyde (0.0293 mol, 4.45 g) was added to a 50 mL three-necked round bottom flask containing 15 mL of ethanol. After stirring well, the mixture was heated to 35° C. to dissolve all the reactants in ethanol. Then, hexahydropyridine (0.01 mol, 1 mL) and ethyl octanoyl acetate (0.029 mol, 6.21 g) were added, and the reaction mixture was heated to reflux, and the reaction was carried out for 1 hour under stirring. After the reaction was completed, the mixture was cooled to room temperature, filtered to obtain a yellow solid, which was then recrystallized with ethanol to obtain 6.3 g product with a yield of 90%, which was identified as compound 21a. 1H-NMR (400 MHz, CDCl$_3$) δ 0.88 (t, 3H), 1.30 (m, 10H), 2.94 (t, 2H), 3.91 (s, 3H), 6.88 (d, 2H), 7.55 (d, 1H), 8.48 (s, 1H).

Synthesis of Intermediate 21b

The intermediate 21a (6.04 g, 0.02 mol) was added to a 100 ml three-necked flask containing 30 ml of tetrahydrofuran, 15 g concentrated hydrochloric acid (35%) was added, and after stirring for 0.5 hours, isoamyl nitrite (2.36 g, 0.02 mol) was added dropwise at a temperature controlled at 5° C. After completion of the dropwise addition, the reaction was continued at 10° C. for 3 hours. After the reaction was completed, the reaction solution was poured into water and extracted with ethyl acetate. The organic phase was collected and washed with water to neutrality. The organic phase was dried, the organic solvent was removed by rotary evaporation, recrystallized with 10 g petroleum ether, and suction filtered at low temperature to obtain 3.31 g white solid with a yield of 50%, which was identified as compound 21b. 1H-NMR (400 MHz, CDCl$_3$) δ 0.88 (t, 3H), 1.30 (m, 8H), 2.94 (t, 2H), 3.91 (s, 3H), 6.88 (d, 2H), 7.55 (d, 1H), 8.48 (s, 1H), 11.31 (s, 1H).

Synthesis of Final Product 21

The above intermediate product 21b (3.31 g, 0.01 mol) and 30 ml of tetrahydrofuran were added to a 100 mL three-neck round bottom flask, then acetyl chloride (0.78 g, 0.01 mol) and triethylamine (1.35 g, 0.013 mol) were added, and the reaction was carried out at room temperature for 1 hour under stirring. The reaction was terminated. After the reaction solution was filtered, the filtrate was poured into water and extracted with ethyl acetate. The organic phase was collected, washed sequentially with dilute hydrochloric acid solution, saturated sodium carbonate solution, and distilled water, and then the organic phase was collected and dried with MgSO$_4$ overnight. After filtration, the organic phase was distilled off under reduced pressure to obtain 3.58 g white solid with a yield of 96.0%, which was identified as compound 21. 1H-NMR (400 MHz, CDCl$_3$) δ 0.88 (t, 3H), 1.30 (m, 8H), 2.94 (t, 2H), 2.23 (s, 3H), 2.39 (s, 3H), 6.88 (d, 2H), 7.55 (d, 1H), 8.48 (s, 1H).

Examples 22 to 30

The method of Example 21 was repeated, and the reaction raw materials were appropriately changed to obtain the compounds 22 to 30 and their NMR data in the following table. The method of Example 1 was repeated, and the reaction raw materials were appropriately changed to obtain the following Compounds 31 to 50 and their NMR data.

| Example | Chemical formula | NMR data |
|---|---|---|
| 22 | 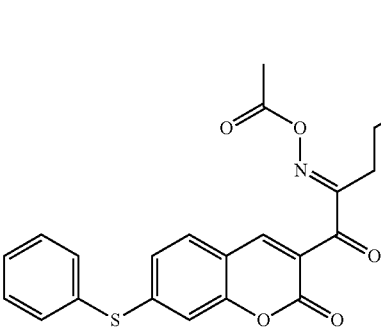 | δ 0.88 (t, 3H), 1.30-1.35 (m, 8H), 1.53-1.56 (t, 2H), 2.28 (s, 3H), 6.88 (d, 2H), 7.55 (d, 1H), 7.19 (d, 1H), 7.25-7.27 (m, 2H), 7.41-7.42 (m, 2H), 8.45 (s, 1H) |
| 23 | 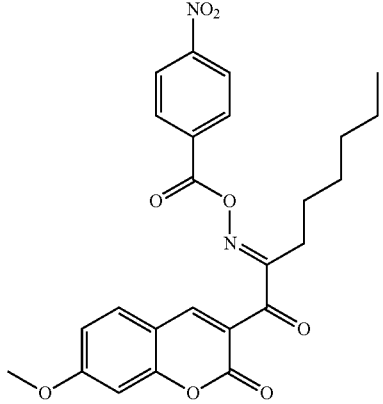 | δ 0.88 (t, 3H), 1.30-1.35 (m, 8H), 1.53-1.56 (t, 2H), 3.83 (s, 3H), 6.88 (d, 1H), 7.55 (d, 1H), 8.48 (s, 1H), 7.25-7.27 (d, 2H), 7.41-7.42 (d, 2H), 8.45 (s, 1H) |
| 24 | 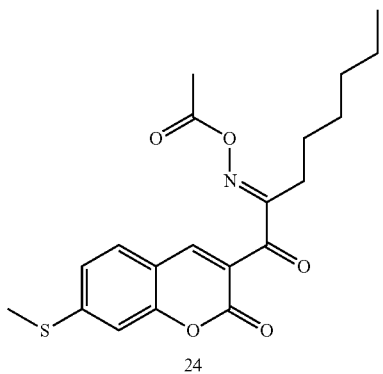 [SMILES: CCCCCC/C(=N\OC(C)=O)C(=O)c1cc2ccc(SC)cc2oc1=O] | δ 0.88 (t, 3H), 1.30-1.35 (m, 8H), 1.53-1.56 (t, 2H), 2.28 (s, 3H), 2.53 (s, 3H), 6.88 (d, 2H), 7.55 (d, 1H), 7.19 (d, 1H) |

-continued

| Example | Chemical formula | NMR data |
| --- | --- | --- |
| 25 | 25 | δ, 1.4-1.6 (m, 11H), 6.88 (d, 2H), 7.55 (d, 1H), 7.19 (s, 1H), 8.45 (s, 1H), 7.19 (d, 1H), 7.22 (d, 1H), 7.25-7.27 (m, 4H), 7.41-7.42 (m, 4H) |
| 26 | 26 | δ, 1.15 (t, 6H), 1.4-1.6 (m, 11H), 2.28 (s, 3H), 3.41 (p, 4H), 7.19 (s, 1H), 8.45 (s, 1H), 7.19 (d, 1H), 7.22 (d, 1H) |
| 27 | 27 | δ, 1.15 (t, 6H), 0.88 (t, 3H), 1.30-1.35 (m, 8H), 1.53-1.56 (t, 2H), 2.28 (s, 3H), 3.41 (p, 4H), 7.19 (s, 1H), 8.45 (s, 1H), 7.19 (d, 1H), 7.22 (d, 1H) |
| 28 | 28 | δ, 1.43-1.80 (m, 11H), 3.42 (m, 1H), 2.28 (s, 3H), 7.19 (s, 1H), 8.45 (s, 1H), 7.19 (d, 1H), 7.22 (d, 1H), 7.22 (d, 1H), 7.25-7.27 (m, 2H), 7.41-7.42 (m, 2H) |

-continued

| Example | Chemical formula | NMR data |
|---|---|---|
| 29 | 29 | δ, 0.88 (t, 3H), 1.30-1.35 (m, 8H), 1.53-1.56 (t, 2H), 2.28 (s, 3H), 7.19 (s, 1H), 8.45 (s, 1H), 7.19 (s, 1H) |
| 30 | 30 | δ, 1.4-1.6 (m, 11H), 2.28 (s, 3H), 7.19 (s, 1H), 8.45 (s, 1H), 7.19 (s, 1H) |
| 31 | 31 | δ, 2.28 (s, 3H), 2.34 (s, 3H), 2.53 (s, 3H), 3.11 (s, 3H), 7.19 (s, 1H), 7.54 (s, 1H), 7.63 (s, 1H) |
| 32 | 32 | δ, 1.33 (s, 9H), 1.50 (s, 9H), 2.28 (s, 3H), 2.41 (s, 3H), 7.19 (s, 1H), 7.60 (s, 1H), 8.06 (s, 1H) |
| 33 | 33 | δ, 1.33 (s, 9H), 2.28 (s, 3H), 2.41 (s, 3H), 7.19 (s, 1H), 7.50 (s, 1H), 8.10 (d, 1H), 8.45 (d, 1H) |

-continued

| Example | Chemical formula | NMR data |
| --- | --- | --- |
| 34 | 34 | δ, 1.33 (s, 9H), 2.28 (s, 3H), 2.41 (s, 3H), 7.19-7.25 (m, 4H), 7.41 (d, 2H), 8.10 (d, 1H) |
| 35 | 35 | δ, 1.33 (s, 9H), 2.28 (s, 3H), 2.41 (s, 3H), 2.53 (s, 3H), 7.19 (s, 1H), 7.50 (s, 1H), 8.10 (d, 1H) |
| 36 | 36 | δ, 1.15 (s, 6H), 1.33 (s, 9H), 2.28 (s, 3H), 2.41 (s, 3H) 7.19 (s, 1H), 7.50 (s, 1H), 8.10 (d, 1H) |
| 37 | 37 | δ, 2.28 (s, 3H), 2.34 (s, 3H), 2.53 (s, 3H), 7.19 (s, 1H), 7.54 (s, 1H), 7.63 (s, 1H) |
| 38 | 38 | δ, 2.28 (s, 3H), 2.34 (s, 3H), 2.53 (s, 3H), 7.19 (m, 4H), 7.41 (d, 2H), 7.54 (s, 1H), 7.63 (s, 1H) |

-continued
| Example | Chemical formula | NMR data |
|---|---|---|
| 39 | 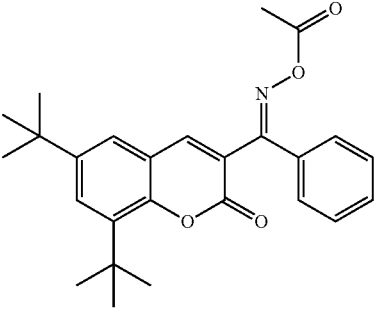<br>39 | δ, 1.33 (s, 9H), 1.50 (s, 9H), 2.28 (s, 3H), 7.19 (m, 4H), 7.41 (d, 2H), 7.60 (s, 1H), 8.06 (s, 1H) |
| 40 | 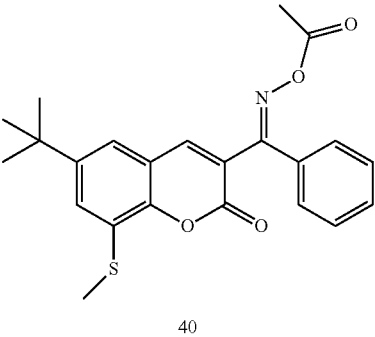 [SMILES: CSc1cc(C(C)(C)C)cc2cc(/C(=N/OC(C)=O)c3ccccc3)c(=O)oc12]<br>40 | δ, 1.33 (s, 9H), 2.28 (s, 3H), 2.53 (s, 3H), 7.19 (m, 4H), 7.41 (d, 2H), 7.50 (s, 1H), 8.10 (d, 1H) |
| 41 | 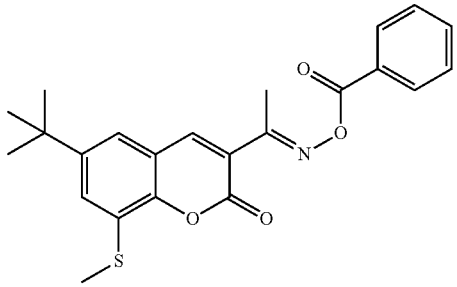<br>41 | δ, 1.33 (s, 9H), 2.41 (s, 3H), 2.53 (s, 3H), 7.19 (m, 4H), 7.41 (d, 2H), 7.50 (s, 1H), 8.10 (d, 1H) |
| 42 | 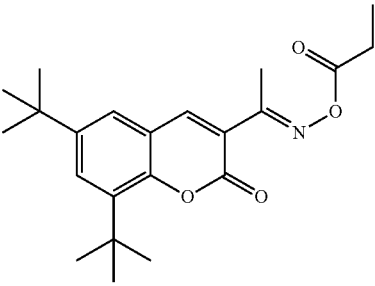<br>42 | δ, 1.09 (s, 3H), 1.33 (s, 9H), 1.50 (s, 9H), 2.07 (m, 2H), 2.41 (s, 3H), 7.19 (s, 1H), 7.60 (s, 1H), 8.06 (s, 1H) |

| Example | Chemical formula | NMR data |
| --- | --- | --- |
| 43 | 43 | δ 1.33 (s, 9H), 1.50 (s, 9H), 2.41 (s, 3H), 7.19 (m, 4H), 7.25 (d, 2H), 7.60 (s, 1H), 8.06 (s, 1H) |
| 44 | 44 | δ, 1.33 (s, 9H), 1.50 (s, 9H), 1.4-1.6 (m, 9H), 2.07 (d, 2H), 2.41 (s, 3H), 7.19 (s, 1H), 7.22 (d, 1H), 8.45 (s, 1H) |
| 45 | 45 | δ, 1.33 (s, 9H), 1.50 (s, 9H), 2.28 (s, 3H), 7.19 (s, 1H), 7.60 (s, 1H), 8.06 (s, 1H) |
| 46 | 46 | δ, 1.33 (s, 9H), 1.50 (s, 9H), 2.28 (s, 3H), 7.19 (s, 1H), 7.41 (d, 4H), 7.60 (s, 1H), 8.06 (s, 1H) |

| Example | Chemical formula | NMR data |
|---|---|---|
| 47 | 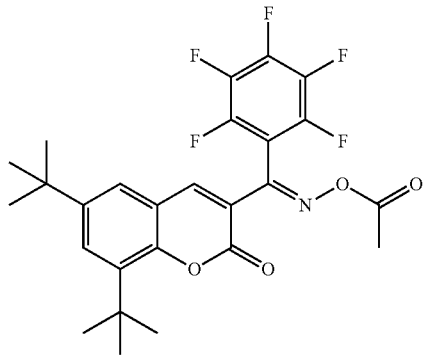<br>47 | δ, 1.33 (s, 9H), 1.50 (s, 9H), 2.28 (s, 3H), 7.19 (s, 1H), 7.60 (s, 1H), 8.06 (s, 1H) |
| 48 | 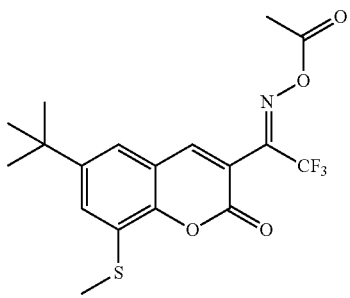<br>48 | δ, 1.33 (s, 9H), 2.28 (s, 3H), 2.53 (s, 3H), 7.19 (s, 1H), 7.50 (s, 1H), 8.10 (d, 1H) |
| 49 | 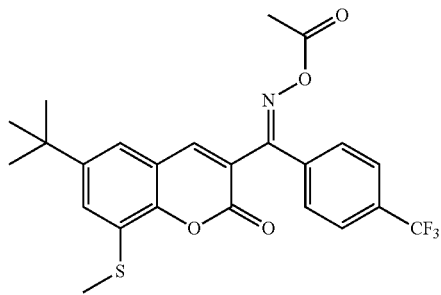<br>49 | δ, 1.33 (s, 9H), 2.28 (s, 3H), 2.53 (s, 3H), 7.19 (s, 1H), 7.25 (d, 4H), 7.50 (s, 1H), 8.10 (d, 1H) |
| 50 | 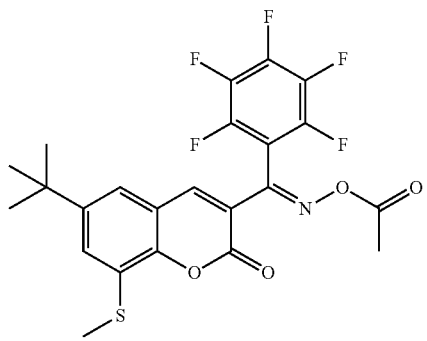<br>50 | δ, 1.33 (s, 9H), 2.28 (s, 3H), 2.41 (s, 3H), 2.53 (s, 3H), 7.19 (s, 1H), 7.50 (s, 1H), 8.10 (d, 1H) |

Thermal Stability Test:

Patent application publication CN104817653A discloses the following compound A. The initial decomposition temperatures of this compound and compounds 1, 3, 21, 28, 31 and 32 of the present invention are shown in the following table:

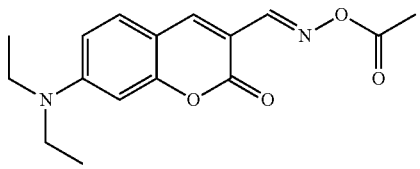

A

| Compounds | Initial decomposition temperature (° C.) |
|---|---|
| Compound 1 | 187 |
| Compound 3 | 190 |
| Compound 21 | 165 |
| Compound 28 | 175 |
| Compound 31 | 170 |
| Compound 32 | 200 |
| Compound A | 150 |

As can be seen from the above table, the initial decomposition temperatures of compounds 1, 3, 21, 28, 31 and 32 according to the present invention are significantly higher than that of compound A, and therefore they have better thermal stability.

Photosensitive Performance Test:

A Ugra offset plate test strip was used as a mask to test the photosensitivity of the photoinitiator. The sections of the Ugra offset plate test strip is shown in FIG. 1. The Ugra offset plate test strip is divided into 5 control sections, from left to right: continuous density scale section (1); dark-bright micron isoline concentric circle section (2); full-tone dot section (3); ghosting control section (4); highlight, shadow control section (5). The first section: the continuous density scale section is divided into 13 gradients for controlling exposure and development. The second section: dark-bright micron isoline concentric circle section: concentric circle diagram composed of 12 dark-bright micron isoline, which are respectively 4, 6, 8, 10, 12, 15, 20, 25, 30, 40, 55, 70, and used to detect the exposure and development when exposing the PS plate. The third section: full-tone dot section: it consists of 10%-100%, evaluation screens with a range of 10%, which is divided into two rows upper and low, and used to measure the transfer of dots in exposing, proofing and printing, and it can measure the change curve of film dots and offset plate, proofing and printing dots. The fourth section: ghosting control section: it consists of thin lines with a line width of 60 lines/cm and an area ratio of 60%, is divided into 4 small blocks, lines at three angles: 0°, 45°, 90°, and in a quarter of D small block, arranged by short lines at 90° on both sides, 45° in the middle small cube, and 90° above and below. The fifth section: highlight, shadow control section, fine dot section is arranged by the small highlight dots and the corresponding shadow dark dots, which are used to finely control the accuracy of exposure and development of plate. The photosensitive composition containing a photoinitiator was coated on an aluminum substrate, and then exposed and developed. Sensitivity was evaluated from the continuously scale of the obtained image, and accuracy was evaluated from the micro-line test block area, thereby evaluating the pros and cons of the photosensitive composition formula.

Specifically, the photosensitivity of the compound of formula (I) was tested according to the following steps.

(1) A photosensitive composition containing a photoinitiator was prepared according to the following composition:

| | |
|---|---|
| acrylate resin | 200 parts by mass |
| dipentaerythritol hexaacrylate | 100 parts by mass |
| photoinitiator | 5 parts by mass |
| crystal violet dye | 5 parts by mass |
| butanone (solvent) | 900 parts by mass |

The photoinitiator in the above composition was selected from a coumarin ketooxime ester compound represented by the formula (I) of the present invention or a photoinitiator known in the art (for comparison). Acrylate resin is a resin purchased under the trade name of FS2600K from Shanghai Feelshun International Trade Co., Ltd., having a functionality of 2 and a number average molecular weight of 1400. Dipentaerythritol hexaacrylate was a product purchased under the trade name of GM66G0C from Shanghai Feelshun International Trade Co., Ltd. Crystal violet dye was a product purchased under the trade name hexamethylrosaniline hydrochloride from Shanghai Sinopharm.

Photosensitive Performance Test (2) each of the above compositions was stirred and mixed under yellow light, and spin-coated using a centrifuge on a PS aluminum plate substrate treated in advance and meeting the following conditions:

| | |
|---|---|
| Aluminum plate substrate size: | 1030 mm × 800 mm |
| Aluminum plate substrate thickness: | 0.28-0.3 mm |
| Grit specification: | Ra = 0.5-0.6 µm |
| | Rh = 0.3-0.35 µm |
| Weight of anode oxide film: | 3-3.5 g/m$^2$ |

The rotation speed of the centrifugal coater was controlled so that the coating amount (calculated as solid content) on the aluminum plate substrate was 1.0-2.5 g/m$^2$. After preliminary drying on the centrifugal coater, it was transferred to a blast dryer at 100° C. and dried for 3 minutes to obtain a purple laser CTP original plate. Then, a Ugra test strip was used as a mask to test the photosensitivity of the plate, and after exposure for a period of time, it was developed with a 1% aqueous NaOH solution.

In the exposed area, the photopolymerizable compound underwent a polymerization reaction in the presence of an initiator, and was insoluble in the developing solution, while the non-exposed area was soluble, thus a negative image was obtained. By exposure and development, the sensitivity of photoinitiator was evaluated from the continuous scale of the obtained image. The initiator system sensitivity is characterized by the highest number of gray levels retained (i.e., polymerized) after development. The higher the number of gray levels was, the higher the sensitivity of the test system was. The results are shown in Table 3.

TABLE 3

| Examples/ Comparative Examples | Photoinitiator | photosensitivity (number of gradients) | | | |
|---|---|---|---|---|---|
| | | 365 nm | 385 nm | 395 nm | 405 nm |
| 51 | Compound of Example 1 | 9 | 8 | 7 | 5 |
| 52 | Compound of Example 2 | 10 | 9 | 9 | 8 |
| 53 | Compound of Example 3 | 11 | 10 | 9 | 8 |
| 54 | Compound of Example 4 | 9 | 8 | 8 | 7 |
| 55 | Compound of Example 5 | 10 | 9 | 11 | 10 |
| 56 | Compound of Example 6 | 11 | 10 | 9 | 10 |
| 57 | Compound of Example 7 | 8 | 10 | 9 | 11 |
| 58 | Compound of Example 8 | 9 | 9 | 8 | 10 |
| 59 | Compound of Example 9 | 10 | 9 | 8 | 7 |
| 60 | Compound of Example 10 | 9 | 10 | 9 | 11 |
| 61 | Compound of Example 11 | 8 | 8 | 9 | 10 |
| 62 | Compound of Example 12 | 9 | 8 | 9 | 10 |
| 63 | Compound of Example 13 | 9 | 8 | 8 | 9 |
| 64 | Compound of Example 14 | 10 | 9 | 8 | 7 |
| 65 | Compound of Example 15 | 8 | 9 | 7 | 9 |
| 66 | Compound of Example 16 | 8 | 10 | 9 | 8 |
| 67 | Compound of Example 17 | 8 | 10 | 11 | 10 |
| 68 | Compound of Example 18 | 9 | 8 | 8 | 9 |
| 69 | Compound of Example 19 | 8 | 9 | 9 | 10 |
| 70 | Compound of Example 20 | 8 | 7 | 9 | 8 |
| 71 | Compound of Example 21 | 9 | 11 | 10 | 9 |
| 72 | Compound of Example 22 | 8 | 10 | 9 | 9 |
| 73 | Compound of Example 23 | 8 | 8 | 9 | 7 |
| 74 | Compound of Example 24 | 8 | 9 | 10 | 11 |
| 75 | Compound of Example 25 | 9 | 9 | 8 | 10 |
| 76 | Compound of Example 26 | 8 | 9 | 10 | 11 |
| 77 | Compound of Example 27 | 10 | 8 | 9 | 10 |
| 78 | Compound of Example 28 | 9 | 8 | 10 | 9 |
| 79 | Compound of Example 29 | 10 | 8 | 9 | 10 |
| 80 | Compound of Example 30 | 11 | 8 | 8 | 7 |
| 81 | Compound of Example 31 | 8 | 8 | 9 | 10 |
| 82 | Compound of Example 32 | 9 | 8 | 9 | 10 |
| 83 | Compound of Example 33 | 9 | 8 | 8 | 9 |
| 84 | Compound of Example 34 | 10 | 9 | 8 | 7 |
| 85 | Compound of Example 35 | 8 | 9 | 7 | 9 |
| 86 | Compound of Example 36 | 8 | 10 | 9 | 8 |
| 87 | Compound of Example 37 | 8 | 10 | 11 | 10 |
| 88 | Compound of Example 38 | 9 | 8 | 8 | 9 |
| 89 | Compound of Example 39 | 8 | 9 | 9 | 10 |
| 90 | Compound of Example 40 | 8 | 8 | 9 | 10 |
| 91 | Compound of Example 41 | 9 | 8 | 9 | 10 |
| 92 | Compound of Example 42 | 8 | 10 | 9 | 9 |
| 93 | Compound of Example 43 | 8 | 8 | 9 | 7 |
| 94 | Compound of Example 44 | 8 | 9 | 10 | 11 |
| 95 | Compound of Example 45 | 9 | 9 | 8 | 10 |
| 96 | Compound of Example 46 | 8 | 9 | 10 | 11 |
| 97 | Compound of Example 47 | 10 | 8 | 9 | 10 |
| 98 | Compound of Example 48 | 9 | 8 | 10 | 9 |
| 99 | Compound of Example 49 | 8 | 10 | 9 | 9 |
| 100 | Compound of Example 50 | 8 | 10 | 9 | 9 |
| Comparative example 1 | OXE-01 | 8 | 7 | 5 | 3 |
| Comparative example 2 | OXE-02 | 9 | 7 | 6 | 3 |

In Table 3, OXE-01 represents 1-[4-(phenylthio)phenyl]-1,2-octanedione 2-(O-benzoyloxime), and OXE-02 represents 1-(6-O-methylbenzoyl-9-ethylcarbazol-3-yl)-(3-ethyl ketone)-1-oxime acetate, the structural formulas are as follows:

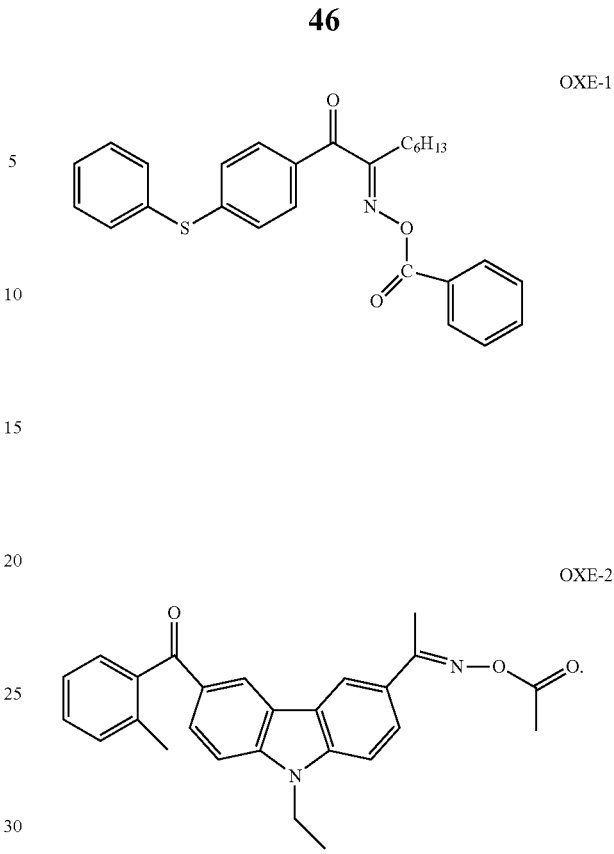

It can be clearly seen from the experimental results in Table 3 that the gray scale numbers of the photoinitiators 1 to 50 of the present invention at 365 nm, 385 nm, 395 nm and 405 nm are higher than those of commercially available photoinitiators OXE-01 and OXE-02. In other words, the coumarin (keto) oxime ester photoinitiators of the present invention have superior photosensitivity at wavelengths of 365 nm, 385 nm, 395 nm and 405 nm, and are suitable for UV-LED light sources of 365 nm, 385 nm, 395 nm, 405 nm.

In summary, the coumarin (keto) oxime ester photoinitiators represented by formula (I) of the present invention have good photosensitivity at wavelengths of 365 nm, 385 nm, 395 nm, and 405 nm, which is better than currently commercially available ketoxime ester photoinitiators such as OXE-01 and OXE-02. In addition, the production process of the compounds disclosed in the present invention is simple and has high yield, and is very suitable for industrial production. These compounds have good compatibility with UV-LED light sources of 365 nm, 385 nm, 395 nm, and 405 nm, and can be widely used as photoinitiators in fields involving UV-LED light curing such as coatings, inks, microelectronics, printing and the like. Such substances have good market prospects. In view of the limited variety of photoinitiators currently applicable to UV-LEDs, the promotion and application of UV-LED light sources in the field of ultraviolet curing is limited to a certain extent. Therefore, the photoinitiator of the present invention can contribute to promote the widespread application of green and environmentally friendly UV-LED light sources in the UV light curing industry.

The invention claimed is:
1. A coumarin (keto) oxime ester compound of formula (I):

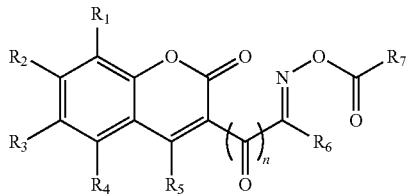

wherein:

n is 0;

$R_1$, $R_3$, and $R_4$, independently represent hydrogen, halogen, nitro, hydroxyl, mercapto, carboxyl, $C_1$-$C_8$ carboxylate ester group, sulfonic acid group, amino, cyano, $C_1$-$C_{20}$ alkyl, $C_2$-$C_{20}$ alkenyl, $C_2$-$C_{20}$ alkynyl, $C_3$-$C_{20}$ cycloalkyl, $C_4$-$C_{20}$ cycloalkylalkyl, $C_1$-$C_{20}$ alkoxy, $C_2$-$C_{20}$ alkenyloxy, $C_2$-$C_{20}$ alkynyloxy, $C_3$-$C_{20}$ cycloalkoxy, $C_4$-$C_{20}$ cycloalkylalkoxy, $C_1$-$C_{20}$ alkylthio, $C_2$-$C_{20}$ alkenylthio, $C_2$-$C_{20}$ alkynylthio, $C_3$-$C_{20}$ cycloalkylthio, $C_4$-$C_{20}$ cycloalkylalkylthio, $C_6$-$C_{18}$ aryl, $C_6$-$C_{18}$ aryloxy and $C_6$-$C_{18}$ arylthio, wherein the aforementioned amino, $C_1$-$C_{20}$ alkyl, $C_2$-$C_{20}$ alkenyl, $C_2$-$C_{20}$ alkynyl, $C_3$-$C_{20}$ cycloalkyl, $C_4$-$C_{20}$ cycloalkylalkyl, $C_1$-$C_{20}$ alkoxy, $C_2$-$C_{20}$ alkenyloxy, $C_2$-$C_{20}$ alkynyloxy, $C_3$-$C_{20}$ cycloalkoxy, $C_4$-$C_{20}$ cycloalkylalkoxy, $C_1$-$C_{20}$ alkylthio, $C_2$-$C_{20}$ alkenylthio, $C_2$-$C_{20}$ alkynylthio, $C_3$-$C_{20}$ cycloalkylthio, $C_4$-$C_{20}$ cycloalkylalkylthio, $C_6$-$C_{18}$ aryl, $C_6$-$C_{18}$ aryloxy and $C_6$-$C_{18}$ arylthio may be optionally substituted with one or more groups independently selected from the group consisting of: halogen, nitro, hydroxy, mercapto, carboxyl, sulfonic acid group, amino, cyano, $C_1$-$C_6$ alkyl, $C_1$-$C_6$ alkoxy, $C_1$-$C_6$ alkylthio, $C_2$-$C_6$ alkenyl and $C_2$-$C_6$ alkynyl, $R_2$ represents halogen, nitro, hydroxyl, mercapto, carboxyl, $C_1$-$C_8$ carboxylate ester group, sulfonic acid group, amino, cyano, $C_1$-$C_{20}$ alkyl, $C_2$-$C_{20}$ alkenyl, $C_2$-$C_{20}$ alkynyl, $C_3$-$C_{20}$ cycloalkyl, $C_4$-$C_{20}$ cycloalkylalkyl, $C_1$-$C_{20}$ alkoxy, $C_2$-$C_{20}$ alkenyloxy, $C_2$-$C_{20}$ alkynyloxy, $C_3$-$C_{20}$ cycloalkoxy, $C_4$-$C_{20}$ cycloalkylalkoxy, $C_1$-$C_{20}$ alkylthio, $C_2$-$C_{20}$ alkenylthio, $C_2$-$C_{20}$ alkynylthio, $C_3$-$C_{20}$ cycloalkylthio, $C_4$-$C_{20}$ cycloalkylalkylthio, $C_6$-$C_{18}$ aryl, $C_6$-$C_{18}$ aryloxy and $C_6$-$C_{18}$ arylthio, wherein the aforementioned amino, $C_1$-$C_{20}$ alkyl, $C_2$-$C_{20}$ alkenyl, $C_2$-$C_{20}$ alkynyl, $C_3$-$C_{20}$ cycloalkyl, $C_4$-$C_{20}$ cycloalkylalkyl, $C_1$-$C_{20}$ alkoxy, $C_2$-$C_{20}$ alkenyloxy, $C_2$-$C_{20}$ alkynyloxy, $C_3$-$C_{20}$ cycloalkoxy, $C_4$-$C_{20}$ cycloalkylalkoxy, $C_1$-$C_{20}$ alkylthio, $C_2$-$C_{20}$ alkenylthio, $C_2$-$C_{20}$ alkynylthio, $C_3$-$C_{20}$ cycloalkylthio, $C_4$-$C_{20}$ cycloalkylalkylthio, $C_6$-$C_{18}$ aryl, $C_6$-$C_{18}$ aryloxy and $C_6$-$C_{18}$ arylthio may be optionally substituted with one or more groups independently selected from the group consisting of: halogen, nitro, hydroxy, mercapto, carboxyl, sulfonic acid group, amino, cyano, $C_1$-$C_6$ alkyl, $C_1$-$C_6$ alkoxy, $C_1$-$C_6$ alkylthio, $C_2$-$C_6$ alkenyl and $C_2$-$C_6$ alkynyl;

and $R_5$ is H, $R_6$, and $R_7$ independently represent linear or branched $C_1$-$C_{20}$ alkyl, $C_3$-$C_{10}$ cycloalkyl, $C_4$-$C_{10}$ cycloalkylalkyl, $C_4$-$C_{10}$ alkylcycloalkyl, $C_6$-$C_{20}$ aryl, $C_7$-$C_{20}$ aralkyl and $C_7$-$C_{20}$ alkylaryl, wherein the aforementioned $C_1$-$C_{20}$ alkyl, $C_3$-$C_{10}$ cycloalkyl, $C_4$-$C_{10}$ cycloalkylalkyl, $C_4$-$C_{10}$ alkylcycloalkyl, $C_6$-$C_{20}$ aryl, $C_7$-$C_{20}$ aralkyl and $C_7$-$C_{20}$ alkylaryl are optionally substituted with one or more groups independently selected from the group consisting of: $C_1$-$C_6$ alkyl, $C_1$-$C_6$ alkylthio, $C_1$-$C_6$ alkoxy, halogen, nitro, amino, mono($C_1$-$C_6$ alkyl)amino, di($C_1$-$C_6$ alkyl)amino and mercapto, except for the compound that meets the following definitions: n is 0, $R_1$, $R_2$, $R_3$, $R_4$ and $R_5$ are all H, $R_6$ is methyl, and $R_7$ is n-propyl.

2. The compound according to claim 1, wherein $R_1$, $R_3$, and $R_4$ are independently selected from hydrogen, halogen, nitro, hydroxy, mercapto, carboxyl, $C_1$-$C_6$ carboxylate ester group, sulfonic acid group, amino, cyano, $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkylalkyl, $C_1$-$C_6$ alkoxy, $C_2$-$C_6$ alkenyloxy, $C_2$-$C_6$ alkynyloxy, $C_3$-$C_8$ cycloalkoxy, $C_4$-$C_8$ cycloalkylalkoxy, $C_1$-$C_6$ alkylthio, $C_2$-$C_6$ alkenylthio, $C_2$-$C_6$ alkynylthio, $C_3$-$C_8$ cycloalkylthio, $C_4$-$C_8$ cycloalkylalkylthio, $C_6$-$C_{10}$ aryl, $C_6$-$C_{10}$ aryloxy and $C_6$-$C_{10}$ arylthio, wherein the aforementioned amino, $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkylalkyl, $C_1$-$C_6$ alkoxy, $C_2$-$C_6$ alkenyloxy, $C_2$-$C_6$ alkynyloxy, $C_3$-$C_8$ cycloalkoxy, $C_4$-$C_8$ cycloalkylalkoxy, $C_1$-$C_6$ alkylthio, $C_2$-$C_6$ alkenylthio, $C_2$-$C_6$ alkynylthio, $C_3$-$C_8$ cycloalkylthio, $C_4$-$C_8$ cycloalkylalkylthio, $C_6$-$C_{10}$ aryl, $C_6$-$C_{10}$ aryloxy and $C_6$-$C_{10}$ arylthio may be optionally substituted with one or more groups independently selected from the group consisting of: halogen, nitro, hydroxy, mercapto, carboxyl, sulfonic acid group, amino, cyano, $C_1$-$C_4$ alkyl, $C_1$-$C_4$ alkoxy, $C_1$-$C_4$ alkylthio, $C_2$-$C_4$ alkenyl and $C_2$-$C_4$ alkynyl;

$R_2$ represents halogen, nitro, hydroxy, mercapto, carboxyl, $C_1$-$C_6$ carboxylate ester group, sulfonic acid group, amino, cyano, $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkylalkyl, $C_1$-$C_6$ alkoxy, $C_2$-$C_6$ alkenyloxy, $C_2$-$C_6$ alkynyloxy, $C_3$-$C_8$ cycloalkoxy, $C_4$-$C_8$ cycloalkylalkoxy, $C_1$-$C_6$ alkylthio, $C_2$-$C_6$ alkenylthio, $C_2$-$C_6$ alkynylthio, $C_3$-$C_8$ cycloalkylthio, $C_4$-$C_8$ cycloalkylalkylthio, $C_6$-$C_{10}$ aryl, $C_6$-$C_{10}$ aryloxy and $C_6$-$C_{10}$ arylthio, wherein the aforementioned amino, $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkylalkyl, $C_1$-$C_6$ alkoxy, $C_2$-$C_6$ alkenyloxy, $C_2$-$C_6$ alkynyloxy, $C_3$-$C_8$ cycloalkoxy, $C_4$-$C_8$ cycloalkylalkoxy, $C_1$-$C_6$ alkylthio, $C_2$-$C_6$ alkenylthio, $C_2$-$C_6$ alkynylthio, $C_3$-$C_8$ cycloalkylthio, $C_4$-$C_8$ cycloalkylalkylthio, $C_6$-$C_{10}$ aryl, $C_6$-$C_{10}$ aryloxy and $C_6$-$C_{10}$ arylthio may be optionally substituted with one or more groups independently selected from the group consisting of: halogen, nitro, hydroxy, mercapto, carboxyl, sulfonic acid group, amino, cyano, $C_1$-$C_4$ alkyl, $C_1$-$C_4$ alkoxy, $C_1$-$C_4$ alkylthio, $C_2$-$C_4$ alkenyl and $C_2$-$C_4$ alkynyl;

$R_5$ is H.

3. The compound according to claim 1 or 2, wherein $R_6$ and $R_7$ independently represent linear or branched $C_1$-$C_8$ alkyl, $C_3$-$C_8$ cycloalkyl, $C_4$-$C_8$ cycloalkylalkyl, $C_4$-$C_8$ alkylcycloalkyl, $C_6$-$C_{10}$ aryl, $C_7$-$C_{11}$ aralkyl and $C_7$-$C_{11}$ alkylaryl, wherein the aforementioned $C_1$-$C_8$ alkyl, $C_3$-$C_8$ cycloalkyl, $C_4$-$C_8$ cycloalkylalkyl, $C_4$-$C_8$ alkylcycloalkyl, $C_6$-$C_{10}$ aryl, $C_7$-$C_{11}$ aralkyl and $C_7$-$C_{11}$ alkylaryl are optionally substituted with one or more groups independently selected from the group consisting of: $C_1$-$C_4$ alkyl, $C_1$-$C_4$ alkylthio, $C_1$-$C_4$ alkoxy, halogen, nitro, amino, mono($C_1$-$C_4$ alkyl)amino, di($C_1$-$C_4$ alkyl)amino and mercapto.

4. The compound according to claim 1, wherein
n is 0,
- $R_1$, $R_3$, and $R_4$ are independently selected from hydrogen, halogen, nitro, $C_1$-$C_4$ carboxylate ester group, $C_1$-$C_6$ alkyl, $C_2$-$C_4$ alkenyl, $C_1$-$C_4$ alkoxy, $C_1$-$C_4$ alkylthio, mono($C_1$-$C_4$ alkyl)amino, di($C_1$-$C_4$ alkyl)amino, phenoxy and phenylthio;
- $R_2$ is selected from halogen, nitro, $C_1$-$C_4$ carboxylate ester group, $C_1$-$C_6$ alkyl, $C_2$-$C_4$ alkenyl, $C_1$-$C_4$ alkoxy, $C_1$-$C_4$ alkylthio, mono($C_1$-$C_4$ alkyl)amino, di($C_1$-$C_4$ alkyl)amino, phenoxy and phenylthio;
- $R_6$ is linear or branched $C_1$-$C_6$ alkyl, halo $C_1$-$C_6$ alkyl, $C_5$-$C_6$ cycloalkyl, $C_1$-$C_2$ alkyl substituted with $C_5$-$C_6$ cycloalkyl or phenyl, and the aforementioned phenyl is optionally substituted with one or more groups independently selected from the group consisting of: fluorine, chlorine, bromine, $C_1$-$C_4$ alkyl, $C_1$-$C_4$ alkoxy, $C_1$-$C_4$ alkylthio and halo $C_1$-$C_4$ alkyl, and
- $R_7$ is linear or branched $C_1$-$C_7$ alkyl or phenyl, wherein the phenyl is optionally substituted with one or more groups independently selected from the group consisting of: $C_1$-$C_4$ alkyl, halogen, nitro, amino, mono($C_1$-$C_4$ alkyl)amino and di($C_1$-$C_4$ alkyl)amino.

5. A coumarin (keto) oxime ester compound selected from the group consisting of:

1
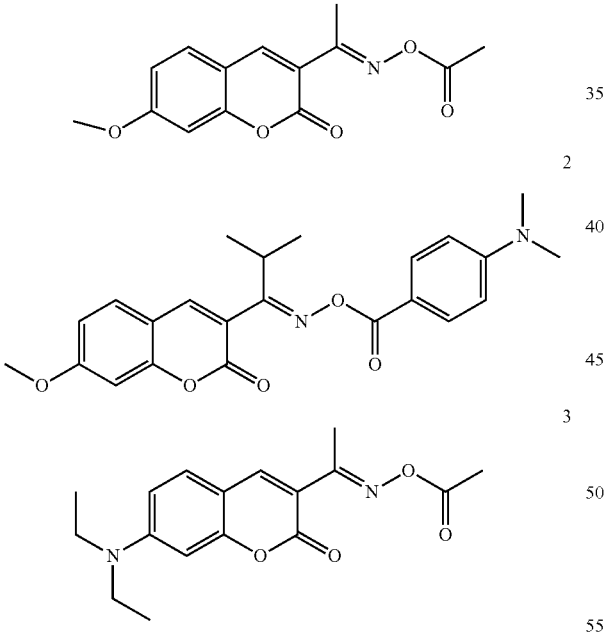

2

3

4
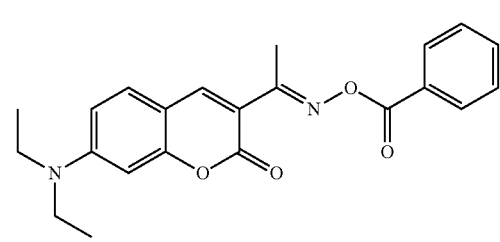

5
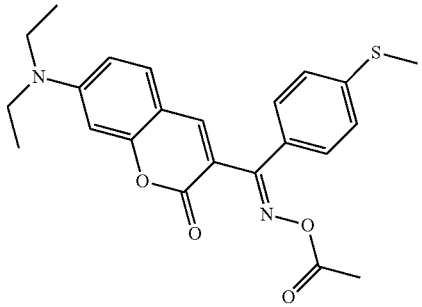

6
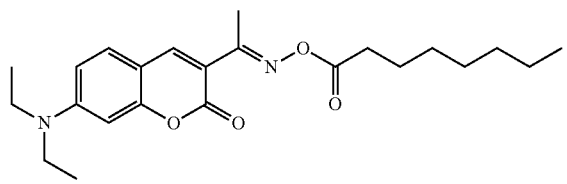

7
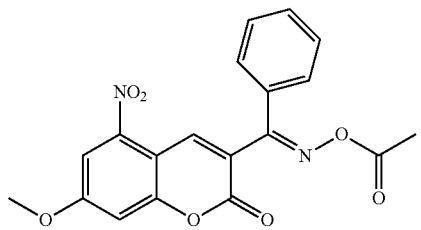

8
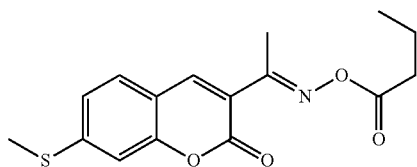

9
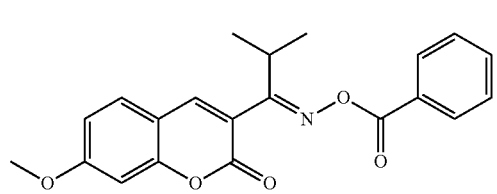

13
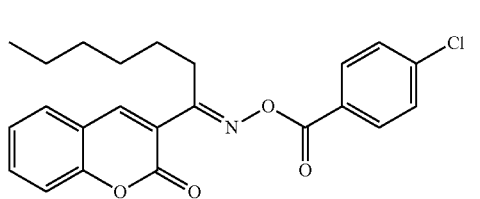

14
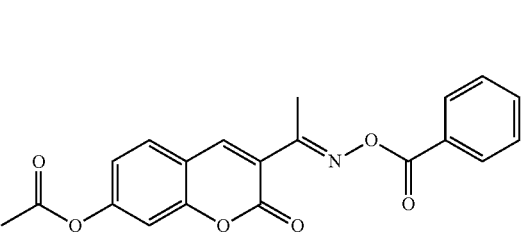

-continued
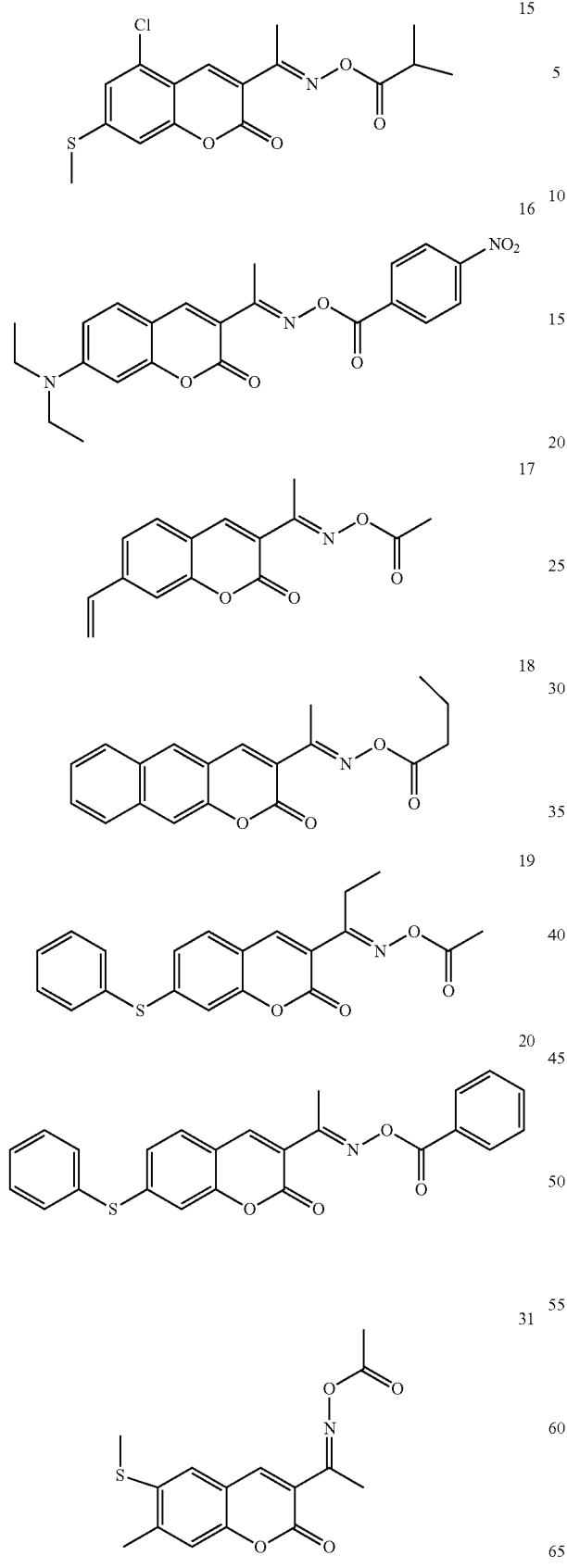
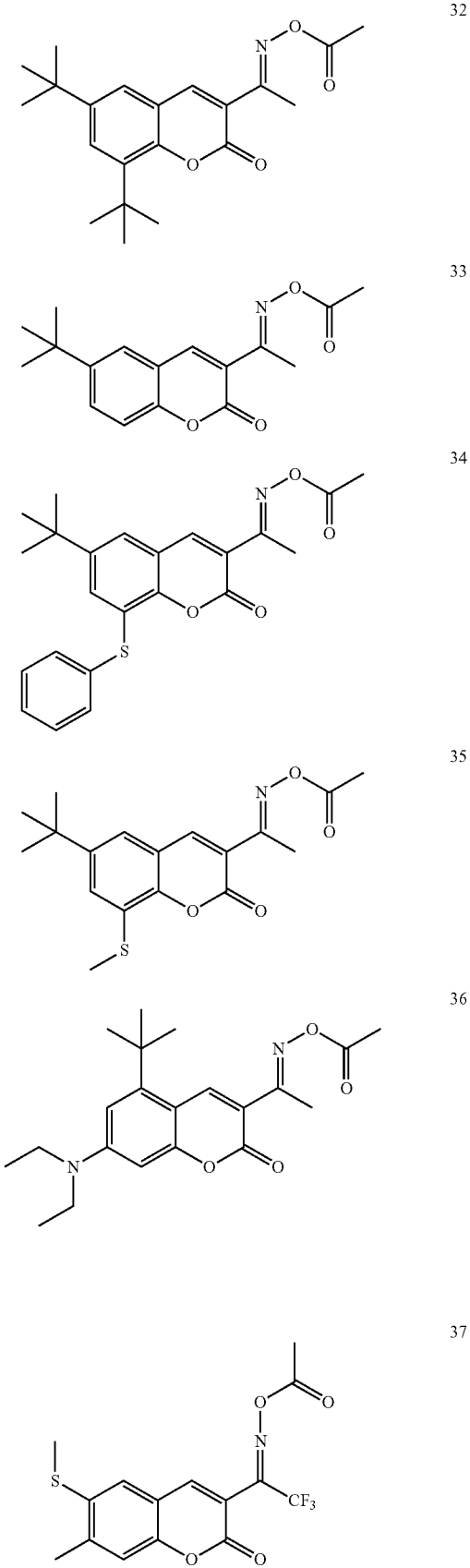

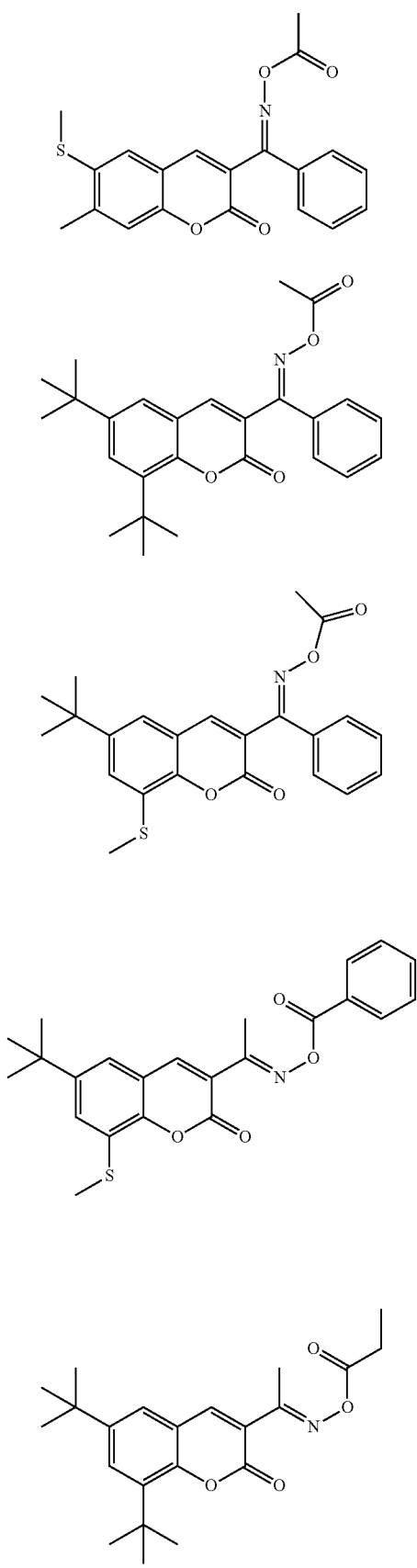
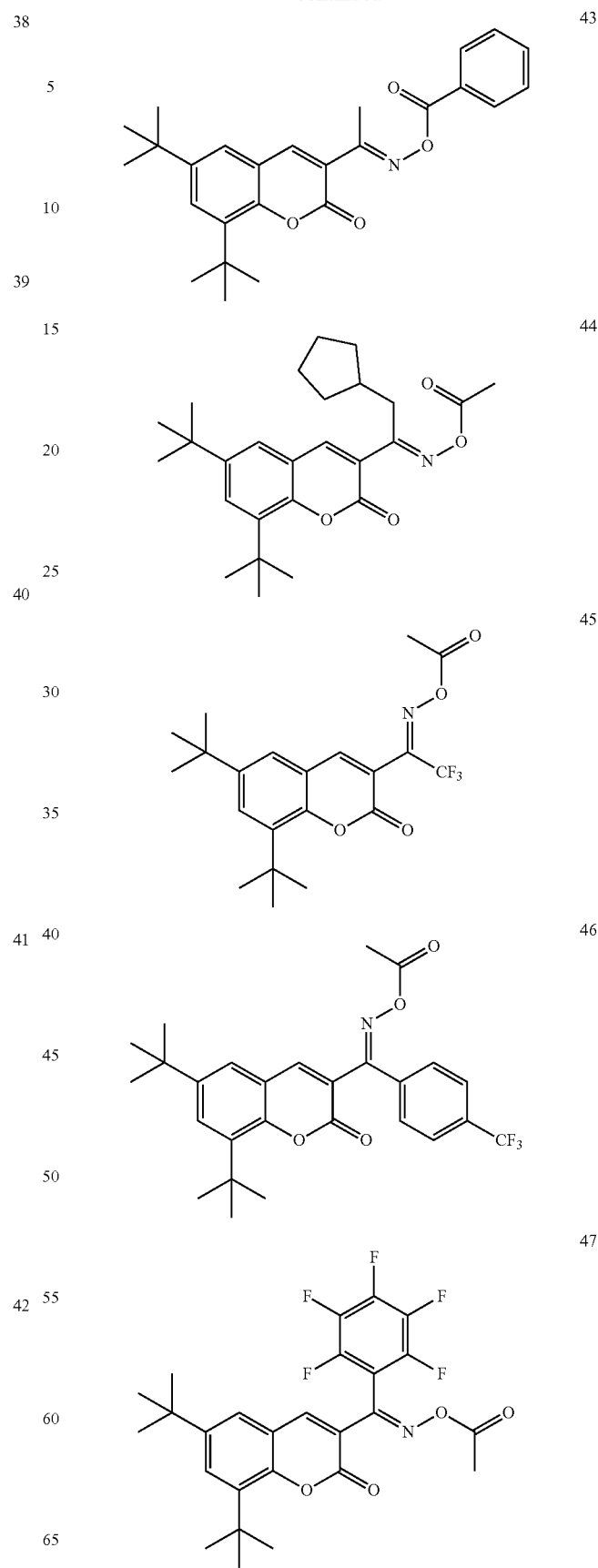

-continued

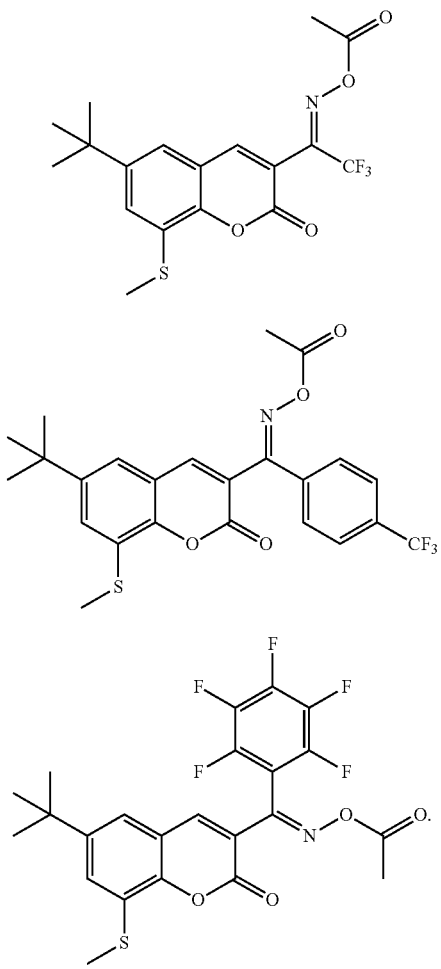

6. The compound according to claim 2, wherein $R_1$, $R_2$, $R_3$, $R_4$ and $R_5$ are independently selected from hydrogen, halogen, nitro, $C_1$-$C_4$ carboxylate ester group, $C_1$-$C_4$ alkyl, $C_2$-$C_4$ alkenyl, $C_1$-$C_4$ alkoxy, $C_1$-$C_4$ alkylthio, mono($C_1$-$C_4$ alkyl)amino, di($C_1$-$C_4$ alkyl)amino, phenoxy and phenylthio.

7. The compound according to claim 3, wherein R6 and R7 are independently selected from linear or branched $C_1$-$C_8$ alkyl, $C_5$-$C_6$ cycloalkyl, $C_1$-$C_4$ alkyl substituted with $C_5$-$C_6$ cycloalkyl, $C_1$-$C_4$ alkyl substituted with phenyl, and phenyl, wherein the aforementioned phenyl each is optionally substituted with one or more groups independently selected from the group consisting of: $C_1$-$C_4$ alkyl, $C_1$-$C_4$ alkylthio, $C_1$-$C_4$ alkoxy, halogen, nitro, amino, mono($C_1$-$C_4$ alkyl)amino, di($C_1$-$C_4$ alkyl)amino and mercapto.

8. The compound according to claim 3, $R_6$ is linear or branched $C_1$-$C_6$ alkyl, $C_5$-$C_6$ cycloalkyl, $C_1$-$C_2$ alkyl substituted with $C_5$-$C_6$ cycloalkyl or phenyl, and the aforementioned phenyl is optionally substituted with one or more groups independently selected from the group consisting of: $C_1$-$C_4$ alkyl, $C_1$-$C_4$ alkylthio, $C_1$-$C_4$ alkoxy, halogen, nitro, amino and mercapto, and $R_7$ is linear or branched $C_1$-$C_7$ alkyl or phenyl, wherein the phenyl is optionally substituted with one or more groups independently selected from the group consisting of: $C_1$-$C_4$ alkyl, halogen, nitro, amino, mono($C_1$-$C_4$ alkyl)amino, di($C_1$-$C_4$ alkyl)amino and mercapto.

* * * * *